US012793225B2

(12) United States Patent
Goldberg et al.

(10) Patent No.: US 12,793,225 B2
(45) Date of Patent: Nov. 10, 2026

(54) AUTOMATIC CONTIGUITY ESTIMATION OF WIDE AREA CIRCUMFERENTIAL ABLATION POINTS

(71) Applicant: Biosense Webster (Israel) Ltd., Yokneam (IL)

(72) Inventors: Stanislav Goldberg, Haifa (IL); Matityahu Amit, Cohav Yair zur Yigal (IL); Yariv Avraham Amos, Tzorit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 1303 days.

(21) Appl. No.: 17/358,820

(22) Filed: Jun. 25, 2021

(65) Prior Publication Data

US 2022/0005198 A1 Jan. 6, 2022

Related U.S. Application Data

(60) Provisional application No. 63/048,412, filed on Jul. 6, 2020.

(51) Int. Cl.
*G06T 7/10* (2017.01)
*A61B 5/364* (2021.01)
(Continued)

(52) U.S. Cl.
CPC ................ *G06T 7/10* (2017.01); *A61B 5/364* (2021.01); *A61B 18/1492* (2013.01);
(Continued)

(58) Field of Classification Search
CPC ............. G06T 7/10; G06T 2207/20036; G06T 2207/20076; G06T 2207/20081;
(Continued)

(56) References Cited

U.S. PATENT DOCUMENTS

| | | | | |
|---|---|---|---|---|
| 9,277,970 | B2 * | 3/2016 | Mansi | A61B 34/10 |
| 2012/0184865 | A1 * | 7/2012 | Harlev | A61B 5/283 600/509 |

(Continued)

FOREIGN PATENT DOCUMENTS

| | | | |
|---|---|---|---|
| EP | 3175807 | A1 | 6/2017 |
| EP | 3944808 | A1 | 2/2022 |

OTHER PUBLICATIONS

Wolf, Michael, et al. Evaluation of left atrial linear ablation using contiguous and optimized radiofrequency lesions: the ALINE study, EP Europace, vol. 20, Issue FI_3, Nov. 2018, pp. f401-f409, https://doi.org/10.1093/europace/eux350 (Year: 2018).*

(Continued)

*Primary Examiner* — Vincent Rudolph
(74) *Attorney, Agent, or Firm* — Volpe Koenig

(57) ABSTRACT

A method is provided by an ablation contiguity engine executed by a processor. The method includes receiving at least wide area circumferential ablation points respective to tissue of an intra-body organ, estimating contiguity of the wide area circumferential ablation points with respect to locations to generate a contiguity estimation, and providing the contiguity estimation with the each of the wide area circumferential ablation points to support treatment of the tissue.

20 Claims, 12 Drawing Sheets

(51) Int. Cl.

| | |
|---|---|
| ***A61B 18/14*** | (2006.01) |
| ***A61B 34/10*** | (2016.01) |
| *A61B 18/00* | (2006.01) |

(52) U.S. Cl.

CPC .... *A61B 34/10* (2016.02); *A61B 2018/00577* (2013.01); *A61B 2018/00839* (2013.01); *A61B 2560/0487* (2013.01); *G06T 2207/20036* (2013.01); *G06T 2207/20076* (2013.01); *G06T 2207/20081* (2013.01); *G06T 2207/20084* (2013.01); *G06T 2207/30048* (2013.01)

(58) Field of Classification Search

CPC .......... G06T 2207/30048; A61B 34/10; A61B 5/364; A61B 18/1492; A61B 2018/00577; A61B 2018/00839; A61B 2560/0487

See application file for complete search history.

(56) References Cited

U.S. PATENT DOCUMENTS

| | | | | |
|---|---|---|---|---|
| 2012/0232417 | A1* | 9/2012 | Zhang .................. | A61B 5/7282 600/521 |
| 2017/0156792 | A1* | 6/2017 | Ziv-Ari .................. | G16H 40/63 |
| 2018/0125575 | A1* | 5/2018 | Schwartz ........... | A61B 18/1492 |
| 2018/0325597 | A1* | 11/2018 | Schwartz ............. | A61B 5/0538 |
| 2019/0090774 | A1* | 3/2019 | Yang ...................... | A61B 5/303 |
| 2021/0085387 | A1* | 3/2021 | Amit .................. | A61B 18/1492 |

OTHER PUBLICATIONS

Wang Y, Zhou G, Chen S, et al. Tailored ablation index for pulmonary vein isolation according to wall thickness within the ablation circle. Pacing & Clinical Electrophysiology. 2021;44(4):575-585. doi: 10.1111/pace. 14125 (Year: 2021).*

Rolf S., et al., Electroanatomical mapping of atrial fibrillation: Review of the current techniques and advances. J Atr Fibrillation. Dec. 31, 2014;7(4):1140. doi: 10.4022/jafib.1140. PMID: 27957132; PMCID: PMC5135200. (Year: 2014).*

De Potter T, et al., The industrialization of ablation: a highly standardized and reproducible workflow for radiofrequency ablation of atrial fibrillation. J Interv Card Electrophysiol. Oct. 2020;59(1):21-27. doi: 10.1007/s10840-019-00622-y. Epub Oct. 17, 2019. PMID: 31625008; PMCID: PMC7508733. (Year: 2019).*

Meyes, R., Lu, et al., Institute of Technologies and Management of the Digital Transformation, & Institute of Information Management in Mechanical Engineering. (2019). Ablation Studies in Artificial Neural Networks. Institute of Technologies and Management of the Digital Transformation. (Year: 2019).*

Communication Pursuant to Article 94(3) EPC issued on Oct. 24, 2023 for European Patent Application No. 21183591.3.

Extended European Search Report d ated Nov. 19, 2021 for European Patent Application No. 21183591.3.

Bacquelin et al., “A novel method for localization and ablation of conduction gaps after wide antral circumferential ablation of pulmonary veins.” Archives of cardiovascular diseases vol. 111, 5: 340-348 (2018).

* cited by examiner

TABLE 900

| SEGMENT | NAME |
|---|---|
| RIGHT POSTERIOR | RPS |
| RIGHT INFERIOR | RIN |
| RIGHT ROOF | RRF |
| RIGHT ANTERIOR | RAN |
| LEFT POSTERIOR | LPS |
| LEFT INFERIOR | LIN |
| LEFT ROOF | LRF |
| LEFT RIDGE | LRG |
| LEFT ANTERIOR | LAN |

USER INTERFACE 901

AUTOMATIC CONTIGUITY ESTIMATION OF WIDE AREA CIRCUMFERENTIAL ABLATION POINTS

CROSS-REFERENCE

This application claims the benefit of U.S. Provisional Patent Application No. 63/048,412 filed on Jul. 6, 2020, which is incorporated by reference as if fully set forth.

FIELD OF TEACHINGS

The present invention is related to an artificial intelligence and machine learning method and system. More particularly, the present invention relates to an artificial intelligence and machine learning algorithm that executes automatic contiguity estimations of wide area circumferential ablation (WACA) points.

BACKGROUND

Treatments for cardiac conditions often require heart imaging (i.e., imaging cardiac tissue, chambers, veins, arteries and/or pathways, which is also known as cardiac scanning or cardiac imaging) and subsequent ablation (i.e., removal or destruction of the imaged cardiac tissue, chambers, veins, arteries and/or pathways). In an example, the cardiac condition of atrial fibrillation can be imaged and treated using atrial fibrillation ablation. A specific type of atrial fibrillation ablation is wide area circumferential ablation (WACA).

Conventionally, during the heart mapping phase, WACA achieves right and left pulmonary vein isolation, point by point (e.g., WACA points), to make a circular ring around the left and right pulmonary veins (e.g., in some cases, WACA can extend to a roof of an atria and into a right atria). Yet, WACA is limited by an existence of potential gaps in between the WACA points, an existence of potential gaps in resulting ablation lines, and a dependence by WACA on anatomical structures. For instance, if left untreated during the ablation phase, these gaps could lead to pulmonary vein reconnection and recurrent arrhythmia. To overcome these limitations, conventional methods rely on manual ablation site anatomical segmentation and manual WACA point contiguity estimation by medical professionals. Due to these limitations and in view of conventional manual review methods, a need exists to provide improved methods for predicting potential gaps, providing anatomical segmentation, and providing contiguity estimation for the WACA points.

SUMMARY

According to an embodiment, a method is provided by an ablation contiguity engine executed by at least one processor. The method includes receiving at least a plurality of wide area circumferential ablation points respective to tissue of an intra-body organ, estimating contiguity of the plurality of wide area circumferential ablation points with respect to one or more locations to generate a contiguity estimation, and providing the contiguity estimation with the each of the plurality of wide area circumferential ablation points to support treatment of the tissue.

According to one or more embodiments, the method embodiment above can be implemented as an apparatus, a system, and/or a computer program product.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

Figure 1:
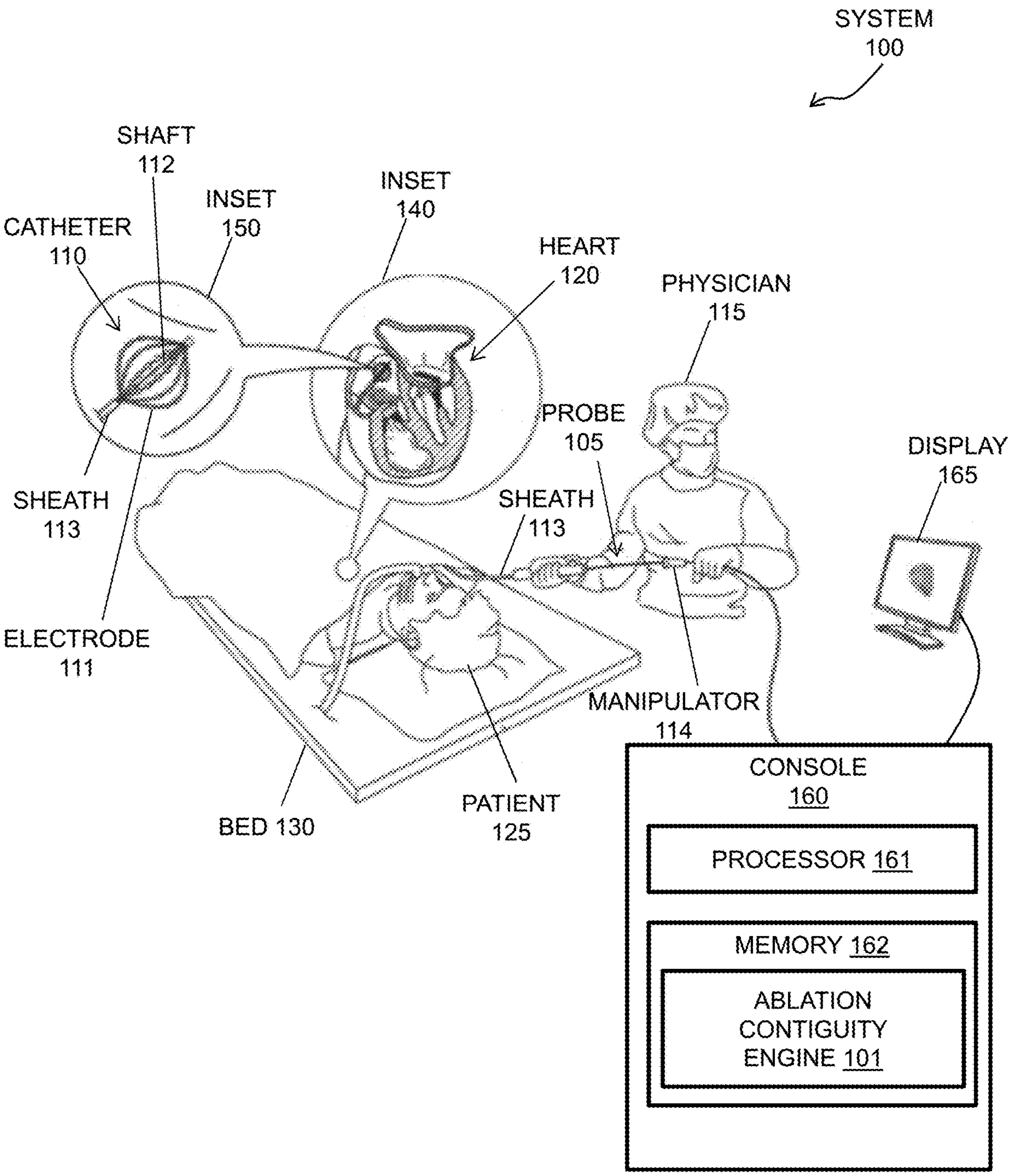
FIG. 1 illustrates a diagram of an exemplary system in which one or more features of the disclosure subject matter can be implemented according to one or more embodiments.

Disclosed herein is an artificial intelligence and machine learning method and system. More particularly, the present teachings relate to an artificial intelligence and machine learning algorithm that executes automatic contiguity estimations of WACA points during a heart mapping phase. For example, the artificial intelligence and machine learning is a processor executable code or software that is necessarily rooted in process operations by, and in processing hardware of, medical device equipment to perform automatic contiguity estimation of the WACA points using one or more of random forest regression, fully connected dense layers, and a convolutional neural network (CNN) plus a dense layer.

According to an embodiment, an ablation contiguity engine (e.g., an implementation of the artificial intelligence and machine learning) that provides a specific multi-step data manipulation of the ablation points (e.g., WACA) points for automatic anatomical segmentation, contiguity estimation, and gap prediction. In this regard, during the heart mapping phase, the ablation contiguity engine generally determines whether an ablation point (e.g., a ablation contiguity engine input) is part of a right WACA or a left WACA (e.g., whether each WACA point is within a left circular ring around the left pulmonary vein (PV) or a right circular ring around the right PV) and classifies the left and right WACA points into nine anatomical structures of for the PVs (e.g., associates each ablation point to one of nine anatomical structures). Note that other types of ablation points can also be part of the ablation contiguity engine 101 input. Further, during the heart mapping phase, the ablation contiguity engine 101 determines whether each of the WACA points is 'good' (i.e., accurate/correct or correct with in a tolerance) to isolate or assist a medical professional when isolating the PVs. To determine good WACA points, the ablation contiguity engine 101 uses the right and left WACA information and anatomical structural classification to predict acute reconnections and redo-locations.

For example, if a physician is unable to isolate the PVs based on the WACA points and therefore cannot find PV reconnections, the physician must take time to manually isolate the PVs so that a WACA session can take place. Clearly, this time is very costly as any manual isolation is a slow process. Advantageously, the ablation contiguity engine 101 seeks to tell the physician in advance where to find the PV reconnections sites (i.e., predicts acute reconnections) to avoid this manual isolation and related lost time. Further, even if there is isolation of the PVs, atrial fibrillation may be repeated after a patient is released from a first WACA session, which requires follow-up ablation sessions. The ablation contiguity engine 101 also advantageously seeks to tell the physician to re-ablate certain areas (i.e., predict redo locations) during the first WACA session.

The technical effects and benefits of the ablation contiguity engine 101 include automatic anatomical segmentation, contiguity estimation, and gap prediction for the WACA points to provide improved image data of cardiac tissue. The improved image data reduces and/or eliminates the potential existence of gaps in between the WACA points and resulting ablation lines and the dependence by WACA on anatomical structures. Thus, the improved image data can then be used for more effective treatment of various cardiovascular diseases, such as reducing or eliminating the potential for these gaps to lead to PV reconnection and recurrent arrhythmia. The ablation contiguity engine 101 can be practically applied, but not limited to, ablation-ultrasound technologies (e.g., atrial fibrillation ablation and WACA), planning and diagnosis of lesions, and assessment and diagnosis of magnetic resonance to address one or more disease states, such as atrial fibrillation, atrial flutter, general electrophysiology, arrhythmias, ventricular fibrillation, and ventricular tachycardia.

According to one or more embodiments, a method is provided by an ablation contiguity engine executed by at least one processor. The method includes receiving at least a plurality of wide area circumferential ablation points respective to tissue of an intra-body organ, estimating contiguity of the plurality of wide area circumferential ablation points with respect to one or more locations to generate a contiguity estimation, and providing the contiguity estimation with the each of the plurality of wide area circumferential ablation points to support treatment of the tissue.

According to one or more embodiments or any of the method embodiments herein, the contiguity estimation can be provided in real time during a procedure via a user interface.

According to one or more embodiments or any of the method embodiments herein, the one or more locations can include a set of points of one or more ablation lines.

According to one or more embodiments or any of the method embodiments herein, the one or more ablation lines can include a left wide area circumferential ablation line and a right wide area circumferential ablation line.

According to one or more embodiments or any of the method embodiments herein, the plurality of wide area circumferential ablation points can be configured in two separate circular rings respective to cardiac tissue of a patient.

According to one or more embodiments or any of the method embodiments herein, the ablation contiguity engine can determine right and left wide area circumferential ablation locations, respective to left and right pulmonary veins of the cardiac tissue, for the plurality of wide area circumferential ablation points.

According to one or more embodiments or any of the method embodiments herein, the ablation contiguity engine can utilize manual annotations of training data and an anatomical structural classifications to determine of the contiguity estimation.

According to one or more embodiments or any of the method embodiments herein, the contiguity estimation can include a probability for contiguity per wide area circumferential ablation point.

According to one or more embodiments or any of the method embodiments herein, the ablation contiguity engine can receive intracardiac electrocardiogram along with the wide area circumferential ablation points.

According to one or more embodiments or any of the method embodiments herein, the ablation contiguity engine can utilize a deep neural network to process features of intracardiac electrocardiogram and the wide area circumferential ablation points when providing the contiguity estimation.

According to one or more embodiments or any of the method embodiments herein, the ablation contiguity engine can receive morphological features and ablation features from the plurality of wide area circumferential ablation points.

According to one or more embodiments or any of the method embodiments herein, the ablation contiguity engine can apply a first fully connected layer to the ablation features and a second fully connected layer to the ablation features and the morphological features to generate an intermediate output.

According to one or more embodiments or any of the method embodiments herein, the ablation contiguity engine can pass the intermediate output through two fully connected networks to provide the contiguity estimation.

According to one or more embodiments, a system is provided. The system includes a memory configured to store processor executable program instructions of an ablation contiguity engine. The system also includes at least one processor configured to execute the program instructions of the ablation contiguity engine to cause the system to receive at least a plurality of wide area circumferential ablation points respective to tissue of an intra-body organ, estimate contiguity of the plurality of wide area circumferential ablation points with respect to one or more locations to generate a contiguity estimation, and provide the contiguity estimation with the each of the plurality of wide area circumferential ablation points to support treatment of the tissue.

According to one or more embodiments or any of the system embodiments herein, the contiguity estimation can be provided in real time during a procedure via a user interface.

According to one or more embodiments or any of the system embodiments herein, the one or more locations can include a set of points of one or more ablation lines.

According to one or more embodiments or any of the system embodiments herein, the one or more ablation lines can include a left wide area circumferential ablation line and a right wide area circumferential ablation line.

According to one or more embodiments or any of the system embodiments herein, the plurality of wide area circumferential ablation points can be configured in two separate circular rings respective to cardiac tissue of a patient.

According to one or more embodiments or any of the system embodiments herein, the ablation contiguity engine can determine right and left wide area circumferential ablation locations, respective to left and right pulmonary veins of the cardiac tissue, for the plurality of wide area circumferential ablation points.

According to one or more embodiments or any of the system embodiments herein, the ablation contiguity engine can utilize manual annotations of training data and an anatomical structural classifications to determine of the contiguity estimation.

According to one or more embodiments or any of the system embodiments herein, the contiguity estimation can include a probability for contiguity per wide area circumferential ablation point.

According to one or more embodiments or any of the system embodiments herein, the ablation contiguity engine can receive intracardiac electrocardiogram along with the wide area circumferential ablation points.

According to one or more embodiments or any of the system embodiments herein, the ablation contiguity engine can utilize a deep neural network to process features of intracardiac electrocardiogram and the wide area circumferential ablation points when providing the contiguity estimation.

According to one or more embodiments or any of the system embodiments herein, the ablation contiguity engine can receive morphological features and ablation features from the plurality of wide area circumferential ablation points.

According to one or more embodiments or any of the system embodiments herein, the ablation contiguity engine can apply a first fully connected layer to the ablation features and a second fully connected layer to the ablation features and the morphological features to generate an intermediate output.

According to one or more embodiments or any of the system embodiments herein, the ablation contiguity engine can pass the intermediate output through two fully connected networks to provide the contiguity estimation.

FIG. 1 is a diagram of an exemplary system (e.g., medical device equipment), shown as a system 100, in which one or more features of the subject matter herein can be implemented according to one or more embodiments. All or part of system 100 can be used to collect information (e.g., biometric data and/or a training dataset) and/or used to implement an ablation contiguity engine 101 (e.g., a machine learning and/or an artificial intelligence algorithm) as described herein. The ablation contiguity engine 101 can be considered an artificial intelligence and machine learning as described herein.

The system 100, as illustrated, includes a probe 105 with a catheter 110 (including at least one electrode 111), a shaft 112, a sheath 113, and a manipulator 114. The system 100, as illustrated, also includes a physician 115 (or a medical professional or clinician, or a user in general), a heart 120, a patient 125, and a bed 130 (or a table). Note that insets 140 and 150 show the heart 120 and the catheter 110 in greater detail. The system 100 also, as illustrated, includes a console 160 (including one or more processors 161 and memories 162) and a display 165. Note further each element and/or item of the system 100 is representative of one or more of that element and/or that item. The example of the system 100 shown in FIG. 1 can be modified to implement the embodiments disclosed herein. The disclosed embodiments can similarly be applied using other system components and settings. Additionally, the system 100 can include additional components, such as elements for sensing electrical activity, wired or wireless connectors, processing and display devices, or the like. While the heart 120 is utilized as a primary example, the heart 120 is representative, as any body part, anatomical structure, and/or intra-body organ can be examined, mapped, and/or diagnosed by the system 100. Thus, the probe 105 having shafts (e.g., the shaft 112) that may be navigated by the physician 115 into a body part or intra-body organ, such as the heart 120, of the patient 125 lying on the bed 130. According to embodiments, multiple probes may be provided; however, for purposes of conciseness, a single probe 105 is described herein. Yet, it is understood that the probe 105 may represent multiple probes.

The system 100 can be utilized to detect, diagnose, and/or treat cardiac conditions (e.g., using the ablation contiguity engine 101). Cardiac conditions, such as cardiac arrhythmias, persist as common and dangerous medical ailments, especially in the aging population. For instance, the system 100 can be part of a surgical system (e.g., CARTO® system sold by Biosense Webster) that is configured to obtain biometric data (e.g., anatomical and electrical measurements of a patient's organ, such as the heart 120) and perform a cardiac ablation procedure. More particularly, treatments for cardiac conditions such as cardiac arrhythmia often require obtaining a detailed mapping of cardiac tissue, chambers, veins, arteries and/or electrical pathways. For example, a prerequisite for performing a catheter ablation (as described herein) successfully is that the cause of the cardiac arrhythmia is accurately located in a chamber of the heart 120. Such locating may be done via an electrophysiological investigation during which electrical potentials are detected spatially resolved with a mapping catheter (e.g., the catheter 110) introduced into the chamber of the heart 120. This electrophysiological investigation, the so-called electro-anatomical mapping, thus provides 3D mapping data which can be displayed on a monitor. In many cases, the mapping function and a treatment function (e.g., ablation) are provided by a single catheter or group of catheters such that the mapping catheter also operates as a treatment (e.g., ablation) catheter at the same time. In this case, the ablation contiguity engine 101 can be directly stored and executed by the catheter 110.

In patients (e.g., the patient 125) with normal sinus rhythm (NSR), the heart (e.g., the heart 120), which includes atrial, ventricular, and excitatory conduction tissue, is electrically excited to beat in a synchronous, patterned fashion. Note that this electrical excitement can be detected as intracardiac electrocardiogram (IC ECG) data or the like.

In patients (e.g., the patient 125) with a cardiac arrhythmia (e.g., atrial fibrillation or aFib), abnormal regions of cardiac tissue do not follow a synchronous beating cycle associated with normally conductive tissue, which is in contrast to patients with NSR. Instead, the abnormal regions of cardiac tissue aberrantly conduct to adjacent tissue, thereby disrupting the cardiac cycle into an asynchronous cardiac rhythm. Note that this asynchronous cardiac rhythm can also be detected as the IC ECG data. Such abnormal conduction has been previously known to occur at various regions of the heart 120, for example, in the region of the sino-atrial (SA) node, along the conduction pathways of the atrioventricular (AV) node, or in the cardiac muscle tissue forming the walls of the ventricular and atrial cardiac chambers. There are other conditions, such as flutter, where the pattern of abnormally conducting tissues lead to reentry paths such that the chamber beats in a regular pattern that can be multiple times the sinus rhythm.

In support of the system 100 detecting, diagnosing, and/or treating cardiac conditions, the probe 105 can be navigated by the physician 115 into the heart 120 of the patient 125 lying on the bed 130. For instance, the physician 115 can insert the shaft 112 through the sheath 113, while manipulating a distal end of the shaft 112 using the manipulator 114 near the proximal end of the catheter 110 and/or deflection from the sheath 113. As shown in an inset 140, the catheter 110 can be fitted at the distal end of the shaft 112. The catheter 110 can be inserted through the sheath 113 in a collapsed state and can be then expanded within the heart 120.

Generally, electrical activity at a point in the heart 120 may be typically measured by advancing the catheter 110 containing an electrical sensor at or near its distal tip (e.g., the at least one electrode 111) to that point in the heart 120, contacting the tissue with the sensor and acquiring data at that point. One drawback with mapping a cardiac chamber using a catheter type containing only a single, distal tip electrode is the long period of time required to accumulate data on a point-by-point basis over the requisite number of points required for a detailed map of the chamber as a whole. Accordingly, multiple-electrode catheters (e.g., the catheter 110) have been developed to simultaneously measure electrical activity at multiple points in the heart chamber.

The catheter 110, which can include the at least one electrode 111 and a catheter needle coupled onto a body thereof, can be configured to obtain biometric data, such as electrical signals of an intra-body organ (e.g., the heart 120), and/or to ablate tissue areas of thereof (e.g., a cardiac chamber of the heart 120). Note that the electrodes 111 are representative of any like elements, such as tracking coils, piezoelectric transducer, electrodes, or combination of elements configured to ablate the tissue areas or to obtain the biometric data. According to one or more embodiments, the catheter 110 can include one or more position sensors that used are to determine trajectory information. The trajectory information can be used to infer motion characteristics, such as the contractility of the tissue.

Biometric data (e.g., patient biometrics, patient data, or patient biometric data) can include one or more of local activation times (LATs), electrical activity, topology, bipolar mapping, reference activity, ventricle activity, dominant frequency, impedance, data at a multiplicity of points (e.g., such as WACA points), and/or the like. The LAT can be a point in time of a threshold activity corresponding to a local activation, calculated based on a normalized initial starting point. Electrical activity can be any applicable electrical signals that can be measured based on one or more thresholds and can be sensed and/or augmented based on signal to noise ratios and/or other filters. A topology can correspond to the physical structure of a body part or a portion of a body part and can correspond to changes in the physical structure relative to different parts of the body part or relative to different body parts. A dominant frequency can be a frequency or a range of frequency that is prevalent at a portion of a body part and can be different in different portions of the same body part. For example, the dominant frequency of a PV of a heart can be different than the dominant frequency of the right atrium of the same heart. Impedance can be the resistance measurement at a given area of a body part.

Examples of biometric data include, but are not limited to, patient identification data, IC ECG data, bipolar intracardiac reference signals, anatomical and electrical measurements, trajectory information, body surface (BS) ECG data, historical data, brain biometrics, blood pressure data, ultrasound signals, radio signals, audio signals, a two- or three-dimensional image data, blood glucose data, and temperature data. The biometrics data can be used, generally, to monitor, diagnosis, and treatment any number of various diseases, such as cardiovascular diseases (e.g., arrhythmias, cardiomyopathy, and coronary artery disease) and autoimmune diseases (e.g., type I and type II diabetes). Note that BS ECG data can include data and signals collected from electrodes on a surface of a patient, IC ECG data can include data and signals collected from electrodes within the patient, and ablation data can include data and signals collected from tissue that has been ablated. Further, BS ECG data, IC ECG data, and ablation data, along with catheter electrode position data, can be derived from one or more procedure recordings.

For example, the catheter 110 can use the electrodes 111 to implement intravascular ultrasound and/or MRI catheterization to image the heart 120 (e.g., obtain and process the biometric data). Inset 140 shows the catheter 110 in an enlarged view, inside a cardiac chamber of the heart 120. Although the catheter 110 is shown to be a point catheter, it will be understood that any shape that includes one or more elements (e.g., electrodes 111, tracking coils, piezoelectric transducer, etc.) can be used to implement the exemplary embodiments disclosed herein.

Examples of the catheter 110 include, but are not limited to, a linear catheter with multiple electrodes, a balloon catheter including electrodes dispersed on multiple spines that shape the balloon, a lasso or loop catheter with multiple electrodes, a contact-force sensing catheter, or any other applicable shape or type. Linear catheters can be fully or partially elastic such that it can twist, bend, and or otherwise change its shape based on received signal and/or based on application of an external force (e.g., cardiac tissue) on the linear catheter. The balloon catheter can be designed such that when deployed into a patient's body, its electrodes can be held in intimate contact against an endocardial surface. As an example, a balloon catheter can be inserted into a lumen, such as a PV. The balloon catheter can be inserted into the PV in a deflated state, such that the balloon catheter does not occupy its maximum volume while being inserted into the PV. The balloon catheter can expand while inside the PV, such that those electrodes on the balloon catheter are in contact with an entire circular section of the PV. Such contact with an entire circular section of the PV, or any other lumen, can enable efficient imaging and/or ablation.

According to other examples, body patches and/or body surface electrodes may also be positioned on or proximate to a body of the patient 125. The catheter 110 with the one or more electrodes 111 can be positioned within the body (e.g., within the heart 120) and a position of the catheter 110 can be determined by the 100 system based on signals transmitted and received between the one or more electrodes 111 of the catheter 110 and the body patches and/or body surface electrodes. Additionally, the electrodes 111 can sense the biometric data from within the body of the patient 125, such as within the heart 120 (e.g., the electrodes 111 sense the electrical potential of the tissue in real time). The biometric data can be associated with the determined position of the catheter 110 such that a rendering of the patient's body part (e.g., the heart 120) can be displayed and show the biometric data overlaid on a shape of the body part.

The probe 105 and other items of the system 100 can be connected to the console 160. The console 160 can include any computing device, which employs the machine learning and/or an artificial intelligence algorithm (represented as the ablation contiguity engine 101). According to an exemplary embodiment, the console 160 includes the one or more processors 161 (any computing hardware) and the memory 162 (any suitable non-transitory tangible, volatile, and/or non-volatile media, such as random-access memory or a hard disk drive), where the one or more processors 161 execute computer instructions with respect the ablation contiguity engine 101 and the memory 162 stores these instructions for execution by the one or more processors 161. For instance, the console 160 can be configured to receive and process the biometric data and determine if a given tissue area conducts electricity.

In some embodiments, the console 160 can be further programmed by the ablation contiguity engine 101 (in software) to carry out the functions described. For instance, the ablation contiguity engine 101 can include an algorithm (described herein with respect to FIG. 3), that receives biometric data and/or WACA points acquired by the catheter 110 as it is maneuvered within the anatomical structure and provides a map. Once the map is generated, the ablation contiguity engine 101 can receive inputs representing user modifications of the map, such as through existing user interface and/or a specialized user interface of the ablation contiguity engine 101. Generally, the ablation contiguity engine 101 can provide one or more user interfaces, such as on behalf of the operating system or other application and/or directly as needed. The user interfaces include, but are not limited to, internet browsers, graphic user interfaces (GUIs), window interfaces, and/or other visual interfaces for applications, operating systems, file folders, and the like. According to one or more embodiments, the ablation contiguity engine 101 can be external to the console 160 and can be located, for example, in the catheter 110, in an external device, in a mobile device, in a cloud-based device, or can be a standalone processor. In this regard, the ablation contiguity engine 101 can be transferable/downloaded in electronic form, over a network. It should be understood that ablation contiguity engine 101 can be implemented as a general purpose computer, a processor, a processor core, or fixed function circuitry, as a program, software, or firmware, stored in a non-transitory computer readable medium or in another medium, executable by a general purpose computer, a processor, or as a combination of software executing on a processor or fixed function circuitry.

In an example, the console 160 can be any computing device, as noted herein, including software (e.g., the ablation contiguity engine 101) and/or hardware (e.g., the processor 161 and the memory 162), such as a general-purpose computer, with suitable front end and interface circuits for transmitting and receiving signals to and from the probe 105, as well as for controlling the other components of the system 100. For example, the front end and interface circuits include input/output (I/O) communication interfaces that enables the console 160 to receive signals from and/or transfer signals to the at least one electrode 111. The console 160 can include real-time noise reduction circuitry typically configured as a field programmable gate array (FPGA), followed by an analog-to-digital (A/D) ECG or electrocardiograph/electromyogram (EMG) signal conversion integrated circuit. The console 160 can pass the signal from an A/D ECG or EMG circuit to another processor and/or can be programmed to perform one or more functions disclosed herein.

For example, the one or more functions include receiving at least a plurality of WACA points arranged/configured in two separate circular rings respective to cardiac tissue of a patient, estimating contiguity of the two separate circular rings to generate a contiguity estimation, and providing the contiguity estimation with the each of the WACA points to support treatment of the cardiac tissue.

The display 165, which can be any electronic device for the visual presentation of the biometric data, is connected to the console 160. According to an exemplary embodiment, during a procedure, the console 160 can facilitate on the display 165 a presentation of a body part rendering to the physician 115 and store data representing the body part rendering in the memory 162. For instance, maps depicting motion characteristics can be rendered/constructed based on the trajectory information sampled at a sufficient number of points in the heart 120. As an example, the display 165 can include a touchscreen that can be configured to accept inputs from the medical professional 115, in addition to presenting the body part rendering.

In some embodiments, the physician 115 can manipulate the elements of the system 100 and/or the body part rendering using one or more input devices, such as a touch pad, a mouse, a keyboard, a gesture recognition apparatus, or the like. For example, an input device can be used to change a position of the catheter 110, such that rendering is updated. Note that the display 165 can be located at a same location or a remote location, such as a separate hospital or in separate healthcare provider networks.

According to one or more embodiments, the system 100 can also obtain the biometric data using ultrasound, computed tomography (CT), MRI, or other medical imaging techniques utilizing the catheter 110 or other medical equipment. For instance, the system 100 can obtain ECG data and/or anatomical and electrical measurements of the heart 120 (e.g., the biometric data) using one or more catheters 110 or other sensors. More particularly, the console 160 can be connected, by a cable, to BS electrodes, which include adhesive skin patches affixed to the patient 125. The BS electrodes can procure/generate the biometric data in the form of the BS ECG data. For instance, the processor 161 can determine position coordinates of the catheter 110 inside the body part (e.g., the heart 120) of the patient 125. The position coordinates may be based on impedances or electromagnetic fields measured between the body surface electrodes and the electrode 111 of the catheter 110 or other electromagnetic components. Additionally, or alternatively, location pads, which generate magnetic fields used for navigation, may be located on a surface of the bed 130 and may be separate from the bed 130. The biometric data can be transmitted to the console 160 and stored in the memory 162. Alternatively, or in addition, the biometric data may be transmitted to a server, which may be local or remote, using a network as further described herein.

According to one or more exemplary embodiments, the catheter 110 may be configured to ablate tissue areas of a cardiac chamber of the heart 120. Inset 150 shows the catheter 110 in an enlarged view, inside a cardiac chamber of the heart 120. For instance, ablation electrodes, such as the at least one electrode 111, may be configured to provide energy to tissue areas of an intra-body organ (e.g., the heart 120). The energy may be thermal energy and may cause damage to the tissue area starting from the surface of the tissue area and extending into the thickness of the tissue area. The biometric data with respect to ablation procedures (e.g., ablation tissues, ablation locations, etc.) can be considered ablation data.

According to an example, with respect to obtaining the biometric data, a multi-electrode catheter (e.g., the catheter 110) can be advanced into a chamber of the heart 120. Anteroposterior (AP) and lateral fluorograms can be obtained to establish the position and orientation of each of the electrodes. ECGs can be recorded from each of the electrodes 111 in contact with a cardiac surface relative to a temporal reference, such as the onset of the P-wave in sinus rhythm from a BS ECG and/or signals from electrodes 111 of the catheter 110 placed in the coronary sinus. The system, as further disclosed herein, may differentiate between those electrodes that register electrical activity and those that do not due to absence of close proximity to the endocardial wall. After initial ECGs are recorded, the catheter may be repositioned, and fluorograms and ECGs may be recorded again. An electrical map (e.g., via cardiac mapping) can then be constructed from iterations of the process above.

Cardiac mapping can be implemented using one or more techniques. Generally, mapping of cardiac areas such as cardiac regions, tissue, veins, arteries and/or electrical pathways of the heart 120 may result in identifying problem areas such as scar tissue, arrhythmia sources (e.g., electric rotors), healthy areas, and the like. Cardiac areas may be mapped such that a visual rendering of the mapped cardiac areas is provided using a display, as further disclosed herein. Additionally, cardiac mapping (which is an example of heart imaging) may include mapping based on one or more modalities such as, but not limited to LAT, local activation velocity, an electrical activity, a topology, a bipolar mapping, a dominant frequency, or an impedance. Data (e.g., biometric data) corresponding to multiple modalities may be captured using a catheter (e.g., the catheter 110) inserted into a patient's body and may be provided for rendering at the same time or at different times based on corresponding settings and/or preferences of the physician 115.

As an example of a first technique, cardiac mapping may be implemented by sensing an electrical property of heart tissue, for example, LAT, as a function of the precise location within the heart 120. The corresponding data (e.g., biometric data) may be acquired with one or more catheters (e.g., the catheter 110) that are advanced into the heart 120 and that have electrical and location sensors (e.g., the electrodes 111) in their distal tips. As specific examples, location and electrical activity may be initially measured on about 10 to about 20 points on the interior surface of the heart 120. These data points may be generally sufficient to generate a preliminary reconstruction or map of the cardiac surface to a satisfactory quality. The preliminary map may be combined with data taken at additional points to generate a more comprehensive map of the heart's electrical activity. In clinical settings, it is not uncommon to accumulate data at 100 or more sites (e.g., several thousand) to generate a detailed, comprehensive map of heart chamber electrical activity. The generated detailed map may then serve as the basis for deciding on a therapeutic course of action, for example, tissue ablation as described herein, to alter the propagation of the heart's electrical activity and to restore normal heart rhythm.

Further, cardiac mapping can be generated based on detection of intracardiac electrical potential fields (e.g., which is an example of IC ECG data and/or bipolar intracardiac reference signals). A non-contact technique to simultaneously acquire a large amount of cardiac electrical information may be implemented. For example, a catheter type having a distal end portion may be provided with a series of sensor electrodes distributed over its surface and connected to insulated electrical conductors for connection to signal sensing and processing means. The size and shape of the end portion may be such that the electrodes are spaced substantially away from the wall of the cardiac chamber. Intracardiac potential fields may be detected during a single cardiac beat. According to an example, the sensor electrodes may be distributed on a series of circumferences lying in planes spaced from each other. These planes may be perpendicular to the major axis of the end portion of the catheter. At least two additional electrodes may be provided adjacent at the ends of the major axis of the end portion. As a more specific example, the catheter may include four circumferences with eight electrodes spaced equiangularly on each circumference. Accordingly, in this specific implementation, the catheter may include at least 34 electrodes (32 circumferential and 2 end electrodes). As another more specific example, the catheter may include other multi-spline catheters, such as five soft flexible branches, eight radial splines, or a parallel splined pancake turner type (e.g., any of which may have a total of 42 electrodes).

As example of electrical or cardiac mapping, an electrophysiological cardiac mapping system and technique based on a non-contact and non-expanded multi-electrode catheter (e.g., the catheter 110) can be implemented. ECGs may be obtained with one or more catheters 110 having multiple electrodes (e.g., such as between 42 to 122 electrodes). According to this implementation, knowledge of the relative geometry of the probe and the endocardium can be obtained by an independent imaging modality, such as transesophageal echocardiography. After the independent imaging, noncontact electrodes may be used to measure cardiac surface potentials and construct maps therefrom (e.g., in some cases using bipolar intracardiac reference signals). This technique can include the following steps (after the independent imaging step): (a) measuring electrical potentials with a plurality of electrodes disposed on a probe positioned in the heart 120; (b) determining the geometric relationship of the probe surface and the endocardial surface and/or other reference; (c) generating a matrix of coefficients representing the geometric relationship of the probe surface and the endocardial surface; and (d) determining endocardial potentials based on the electrode potentials and the matrix of coefficients.

As another example of electrical or cardiac mapping, a technique and apparatus for mapping the electrical potential distribution of a heart chamber can be implemented. An intra-cardiac multi-electrode mapping catheter assembly can be inserted into the heart 120. The mapping catheter (e.g., the catheter 110) assembly can include a multi-electrode array with one or more integral reference electrodes (e.g., one or the electrodes 111) or a companion reference catheter.

According to one or more exemplary embodiments, the electrodes may be deployed in the form of a substantially spherical array, which may be spatially referenced to a point on the endocardial surface by the reference electrode or by the reference catheter this is brought into contact with the endocardial surface. The preferred electrode array catheter may carry a number of individual electrode sites (e.g., at least 24). Additionally, this example technique may be implemented with knowledge of the location of each of the electrode sites on the array, as well as knowledge of the cardiac geometry. These locations are preferably determined by a technique of impedance plethysmography.

In view of electrical or cardiac mapping and according to another example, the catheter 110 can be a heart mapping catheter assembly that may include an electrode array defining a number of electrode sites. The heart mapping catheter assembly can also include a lumen to accept a reference catheter having a distal tip electrode assembly that may be used to probe the heart wall. The map heart mapping catheter assembly can include a braid of insulated wires (e.g., having 24 to 64 wires in the braid), and each of the wires may be used to form electrode sites. The heart mapping catheter assembly may be readily positionable in the heart 120 to be used to acquire electrical activity information from a first set of non-contact electrode sites and/or a second set of in-contact electrode sites.

Further, according to another example, the catheter 110 that can implement mapping electrophysiological activity within the heart can include a distal tip that is adapted for delivery of a stimulating pulse for pacing the heart or an ablative electrode for ablating tissue in contact with the tip. This catheter 110 can further include at least one pair of orthogonal electrodes to generate a difference signal indicative of the local cardiac electrical activity adjacent the orthogonal electrodes.

As noted herein, the system 100 can be utilized to detect, diagnose, and/or treat cardiac conditions. In example operation, a process for measuring electrophysiologic data in a heart chamber may be implemented by the system 100. The process may include, in part, positioning a set of active and passive electrodes into the heart 120, supplying current to the active electrodes, thereby generating an electric field in the heart chamber, and measuring the electric field at the passive electrode sites. The passive electrodes are contained in an array positioned on an inflatable balloon of a balloon catheter. In preferred embodiments, the array is said to have from 60 to 64 electrodes.

As another example operation, cardiac mapping may be implemented by the system 100 using one or more ultrasound transducers. The ultrasound transducers may be inserted into a patient's heart 120 and may collect a plurality of ultrasound slices (e.g., two dimensional or three-dimensional slices) at various locations and orientations within the heart 120. The location and orientation of a given ultrasound transducer may be known and the collected ultrasound slices may be stored such that they can be displayed at a later time. One or more ultrasound slices corresponding to the position of the probe 105 (e.g., a treatment catheter shown as catheter 110) at the later time may be displayed and the probe 105 may be overlaid onto the one or more ultrasound slices.

In view of the system 100, it is noted that cardiac arrhythmias, including atrial arrhythmias, may be of a multiwavelet reentrant type, characterized by multiple asynchronous loops of electrical impulses that are scattered about the atrial chamber and are often self-propagating (e.g., another example of the IC ECG data). Alternatively, or in addition to the multiwavelet reentrant type, cardiac arrhythmias may also have a focal origin, such as when an isolated region of tissue in an atrium fires autonomously in a rapid, repetitive fashion (e.g., another example of the IC ECG data). Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

For example, aFib occurs when the normal electrical impulses (e.g., another example of the IC ECG data) generated by the sinoatrial node are overwhelmed by disorganized electrical impulses (e.g., signal interference) that originate in the atria veins and PVs causing irregular impulses to be conducted to the ventricles. An irregular heartbeat results and may last from minutes to weeks, or even years. aFib is often a chronic condition that leads to a small increase in the risk of death often due to strokes. A line of treatment for aFib is medication that either slows the heart rate or revert the heart rhythm back to normal. Additionally, persons with aFib are often given anticoagulants to protect them from the risk of stroke. The use of such anticoagulants comes with its own risk of internal bleeding. In some patients, medication is not sufficient and their aFib is deemed to be drug-refractory, i.e., untreatable with standard pharmacological interventions. Synchronized electrical cardioversion may also be used to convert aFib to a normal heart rhythm. Alternatively, aFib patients are treated by catheter ablation.

A catheter ablation-based treatment may include mapping the electrical properties of heart tissue, especially the endocardium and the heart volume, and selectively ablating cardiac tissue by application of energy. Electrical or cardiac mapping (e.g., implemented by any electrophysiological cardiac mapping system and technique described herein) includes creating a map of electrical potentials (e.g., a voltage map) of the wave propagation along the heart tissue or a map of arrival times (e.g., a LAT map) to various tissue located points. Electrical or cardiac mapping (e.g., a cardiac map) may be used for detecting local heart tissue dysfunction. Ablations, such as those based on cardiac mapping, can cease or modify the propagation of unwanted electrical signals from one portion of the heart 120 to another.

The ablation process damages the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. Another example of an energy delivery technique includes irreversible electroporation (IRE), which provides high electric fields that damage cell membranes. In a two-step procedure (e.g., mapping followed by ablation) electrical activity at points within the heart 120 is typically sensed and measured by advancing the catheter 110 containing one or more electrical sensors (e.g., electrodes 111) into the heart 120 and obtaining/acquiring data at a multiplicity of points (e.g., as biometric data generally, or as the WACA points specifically). The WACA points are then utilized to select the endocardial target areas, at which ablation is to be performed. Note that, due to the use of the ablation contiguity engine 101 employed by the exemplary system 100 (e.g., medical device equipment), the data at the multiplicity of points (i.e., the WACA points) is manipulated into improved image data of cardiac tissue that includes locations within a right or a left WACA, classifications into nine anatomical structures, determinations as good or correct, and predictions of acute reconnections and redo-locations. The improved image data can also include stability measurements (e.g., extracted from x, y, z positions during the ablation) and ablation characteristics (e.g., power, impedance, impedance drop, stability, etc.). In accordance with one or more embodiments, the improved image data can include ablation points with associated characteristics, such as force, force over time, impedance, impedance drop, duration, and x, y, z location, and IC ECG data (e.g., optional input to all algorithms).

Cardiac ablation and other cardiac electrophysiological procedures have become increasingly complex as clinicians treat challenging conditions such as atrial fibrillation and ventricular tachycardia. The treatment of complex arrhythmias can now rely on the use of three-dimensional (3D) mapping systems to reconstruct the anatomy of the heart chamber of interest. In this regard, the ablation contiguity engine 101 employed by the system 100 herein manipulates and evaluates the biometric data generally, or the WACA points specifically, to produce improved tissue data that enables more accurate diagnosis, images, scans, and/or maps for treating an abnormal heartbeat or arrhythmia. For example, cardiologists rely upon software, such as the Complex Fractionated Atrial Electrograms (CFAE) module of the CARTO® 3 3D mapping system, produced by Biosense Webster, Inc. (Diamond Bar, Calif.), to generate and analyze ECG data. The ablation contiguity engine 101 of the system 100 enhances this software to generate and analyze the improved biometric data, which further provide multiple pieces of information regarding electrophysiological properties of the heart 120 (including the scar tissue) that represent cardiac substrates (anatomical and functional) of aFib.

Accordingly, the system 100 can implement a 3D mapping system, such as CARTO® 3 3D mapping system, to localize the potential arrhythmogenic substrate of the cardiomyopathy in terms of abnormal ECG detection. The substrate linked to these cardiac conditions is related to the presence of fragmented and prolonged ECGs in the endocardial and/or epicardial layers of the ventricular chambers (right and left). For instance, areas of low or medium voltage may exhibit ECG fragmentation and prolonged activities. Further, during sinus rhythm, areas of low or medium voltage may corresponds to a critical isthmus identified during sustained and organized ventricular arrhythmias (e.g., applies to non-tolerated ventricular tachycardias, as well as in the atria). In general, abnormal tissue is characterized by low-voltage ECGs. However, initial clinical experience in endo-epicardial mapping indicates that areas of low-voltage are not always present as the sole arrhythmogenic mechanism in such patients. In fact, areas of low or medium voltage may exhibit ECG fragmentation and prolonged activities during sinus rhythm, which corresponds to the critical isthmus identified during sustained and organized ventricular arrhythmias, e.g., applies only to non-tolerated ventricular tachycardias. Moreover, in many cases, ECG fragmentation and prolonged activities are observed in the regions showing a normal or near-normal voltage amplitude (>1-1.5 mV). Although the latter areas may be evaluated according to the voltage amplitude, they cannot be considered as normal according to the intracardiac signal, thus representing a true arrhythmogenic substrate. The 3D mapping may be able to localize the arrhythmogenic substrate on the endocardial and/or epicardial layer of the right/left ventricle, which may vary in distribution according to the extension of the main disease.

As another example operation, cardiac mapping may be implemented by the system 100 using one or more multiple-electrode catheters (e.g., the catheter 110). Multiple-electrode catheters are used to stimulate and map electrical activity in the heart 120 and to ablate sites of aberrant electrical activity. In use, the multiple-electrode catheter is inserted into a major vein or artery, e.g., femoral vein, and then guided into the chamber of the heart 120 of concern. A typical ablation procedure involves the insertion of the catheter 110 having at least one electrode 111 at its distal end, into a heart chamber. A reference electrode is provided, taped to the skin of the patient or by means of a second catheter that is positioned in or near the heart or selected from one or the other electrodes 111 of the catheter 110. Radio frequency (RF) current is applied to a tip electrode 111 of the ablating catheter 110, and current flows through the media that surrounds it (e.g., blood and tissue) toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the tip electrode 111 also occurs as a result of conduction from the heated tissue to the electrode itself. If the electrode temperature becomes sufficiently high, possibly above 60 degrees Celsius, a thin transparent coating of dehydrated blood protein can form on the surface of the electrode 111. If the temperature continues to rise, this dehydrated layer can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs, and the catheter 110 must be removed from the body and the tip electrode 111 cleaned.

Figure 2:
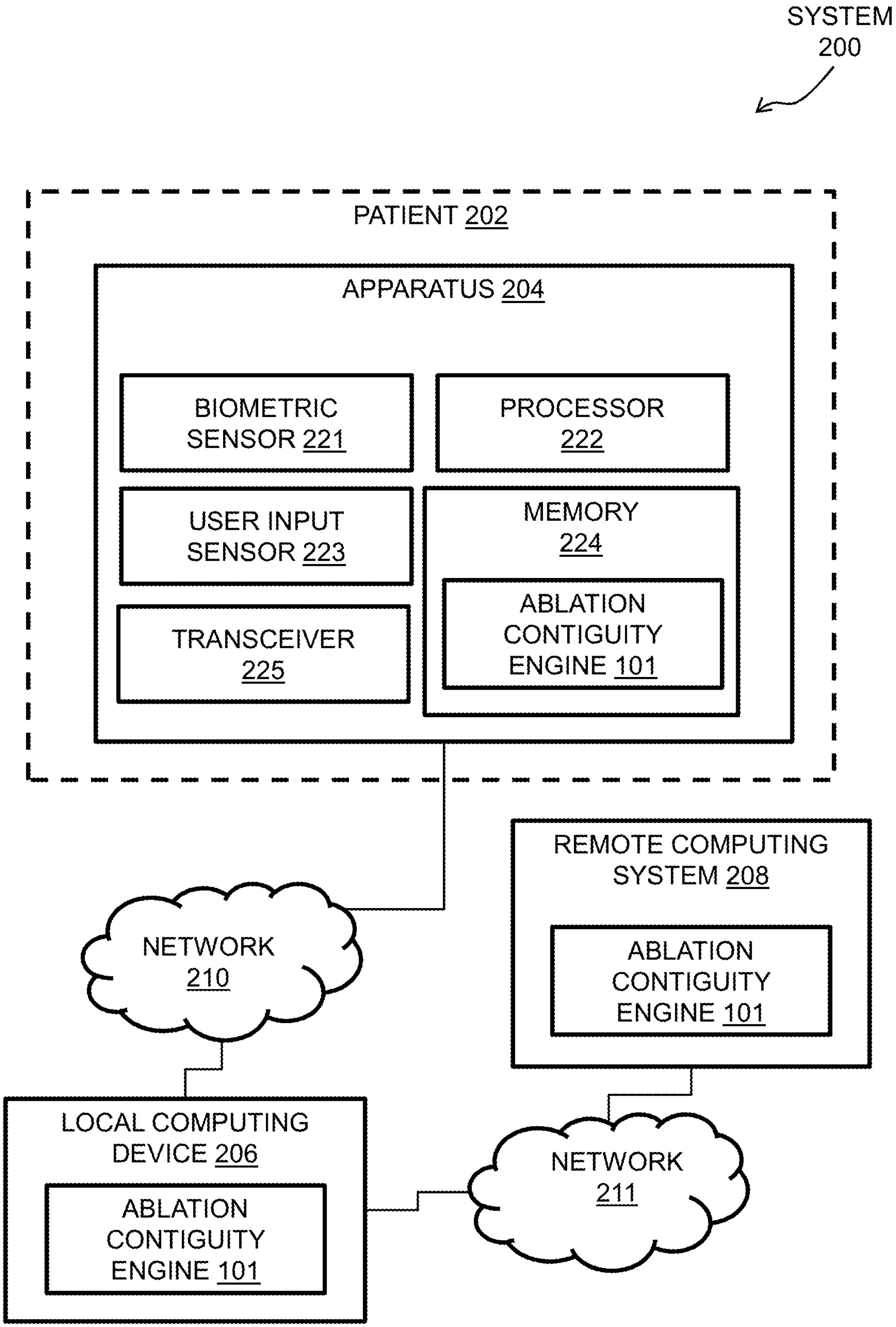
FIG. 2 illustrates a block diagram of an example system for monitoring and communicating patient biometrics according to one or more embodiments.

Turning now to FIG. 2, a diagram of a system 200 in which one or more features of the disclosure subject matter can be implemented is illustrated according to one or more exemplary embodiments. The system 200 includes, in relation to a patient 202 (e.g., an example of the patient 125 of FIG. 1), an apparatus 204, a local computing device 206, a remote computing system 208, a first network 210, and a second network 211. Further, the apparatus 204 can include a biometric sensor 221 (e.g., an example of the catheter 110 of FIG. 1), a processor 222, a user input (UI) sensor 223, a memory 224, and a transceiver 225. Note that the ablation contiguity engine 101 of FIG. 1 is reused in FIG. 2 for ease of explanation and brevity.

According to an embodiment, the apparatus 204 can be an example of the system 100 of FIG. 1, where the apparatus 204 can include both components that are internal to the patient and components that are external to the patient. The apparatus 204 may also include a catheter with one or more electrodes (e.g., the catheter 110 and the electrodes 111 of FIG. 1), a probe (e.g., the probe 105 of FIG. 1), a blood pressure cuff, a weight scale, a bracelet or smart watch biometric tracker, a glucose monitor, a continuous positive airway pressure (CPAP) machine or virtually any device which may provide an input concerning the health or biometrics of the patient 202 (e.g., the patient 125 of FIG. 1). According to another embodiment, the apparatus 204 can be an apparatus that is external to the patient 202 that includes an attachable patch (e.g., that attaches to a patient's skin). According to another embodiment, the apparatus 204 can be internal to a body of the patient 202 (e.g., subcutaneously implantable), where the apparatus 204 can be inserted into the patient 202 via any applicable manner including orally injecting, surgical insertion via a vein or artery, an endoscopic procedure, or a laparoscopic procedure. According to an embodiment, while a single apparatus 204 is shown in FIG. 2, example systems may include a plurality of apparatuses.

Accordingly, the apparatus 204, the local computing device 206, and/or the remote computing system 208 can be programed to execute computer instructions with respect the ablation contiguity engine 101. As an example, the memory 224 stores these instructions for execution by the processor 222 so that the apparatus 204 can receive and process the biometric data via the biometric sensor 201. In this way, the processor 222 and the memory 224 are representative of processors and memories of the local computing device 206 and/or the remote computing system 208.

The apparatus 204, local computing device 206, and/or the remote computing system 208 can be any combination of software and/or hardware that individually or collectively store, execute, and implement the ablation contiguity engine 101 and functions thereof. Further, the apparatus 204, local computing device 206, and/or the remote computing system 208 can be an electronic, computer framework comprising and/or employing any number and combination of computing device and networks utilizing various communication technologies, as described herein. The apparatus 204, local computing device 206, and/or the remote computing system 208 can be easily scalable, extensible, and modular, with the ability to change to different services or reconfigure some features independently of others.

The first network 210 and second network 211 can be a wired network, a wireless network, or include one or more wired and wireless networks. According to an embodiment, the first network 210 is an example of a short-range network (e.g., local area network (LAN), or personal area network (PAN)). Information can be sent, via the first network 210, between the apparatus 204 and the local computing device 206 using any one of various short-range wireless communication protocols, such as Bluetooth, Wi-Fi, Zigbee, Z-Wave, near field communications (NFC), ultra-band, Zigbee, or infrared (IR). Further, the second network 211 is an example of one or more of an Intranet, a local area network (LAN), a wide area network (WAN), a metropolitan area network (MAN), a direct connection or series of connections, a cellular telephone network, or any other network or medium capable of facilitating communication between the local computing device 206 and the remote computing system 208. Information can be sent, via the second network 211, using any one of various long-range wireless communication protocols (e.g., TCP/IP, HTTP, 3G, 4G/LTE, or 5G/New Radio). Note that for either first network 210 and second network 211 wired connections can be implemented using Ethernet, Universal Serial Bus (USB), RJ-11 or any other wired connection and wireless connections can be implemented using Wi-Fi, WiMAX, and Bluetooth, infrared, cellular networks, satellite or any other wireless connection methodology.

In operation, the apparatus 204 can continually or periodically obtain, monitor, store, process, and communicate via first network 210 the biometric data associated with the patient 202. Further, the apparatus 204, local computing device 206, and/the remote computing system 208 are in communication through the first network 210 and second network 211 (e.g., the local computing device 206 can be configured as a gateway between the apparatus 204 and the remote computing system 208). For instance, the apparatus 204 can be an example of the system 100 of FIG. 1 configured to communicate with the local computing device 206 via the first network 210. The local computing device 206 can be, for example, a stationary/standalone device, a base station, a desktop/laptop computer, a smart phone, a smartwatch, a tablet, or other device configured to communicate with other devices via first network 210 and second network 211. The remote computing system 208, implemented as a physical server on or connected to the second network 211 or as a virtual server in a public cloud computing provider (e.g., Amazon Web Services (AWS)®) of the second network 211, can be configured to communicate with the local computing device 206 via the second network 211. Thus, the biometric data associated with the patient 202 can be communicated throughout the system 200.

Elements of the apparatus 204 are now described. The biometric sensor 221 may include, for example, one or more transducers configured to convert one or more environmental conditions into an electrical signal, such that different types of biometric data are observed/obtained/acquired. For example, the biometric sensor 221 can include one or more of an electrode (e.g., the electrode 111 of FIG. 1), a temperature sensor (e.g., thermocouple), a blood pressure sensor, a blood glucose sensor, a blood oxygen sensor, a pH sensor, an accelerometer, and a microphone.

The processor 222, in executing the ablation contiguity engine 101, can be configured to receive, process, and manage the biometric data acquired by the biometric sensor 221, and communicate the biometric data to the memory 224 for storage and/or across the first network 210 via the transceiver 225. As described in more detail herein, the ablation contiguity engine 101 to receive at least a plurality of WACA points arranged/configured in two separate circular rings respective to cardiac tissue of a patient, estimate contiguity of the two separate circular rings to generate a contiguity estimation, and provide the contiguity estimation with the each of the WACA points to support treatment of the cardiac tissue. The ablation contiguity engine 101 produces improved image data of cardiac tissue so that improved images, scans, and/or maps, along with predictions, for treating cardiac conditions can be generated.

Biometric data from one or more other apparatuses 204 can also be received by the processor 222 through the transceiver 225. Also, as described in more detail herein, the processor 222 may be configured to respond selectively to different tapping patterns (e.g., a single tap or a double tap) received from the user input sensor 223, such that different tasks of a patch (e.g., acquisition, storing, or transmission of data) can be activated based on the detected pattern. In some embodiments, the processor 222 can generate audible feedback with respect to detecting a gesture.

The user input sensor 223 includes, for example, a piezoelectric sensor or a capacitive sensor configured to receive a user input, such as a tapping or touching. For example, the user input sensor 223 can be controlled to implement a capacitive coupling, in response to tapping or touching a surface of the apparatus 204 by the patient 202. Gesture recognition may be implemented via any one of various capacitive types, such as resistive capacitive, surface capacitive, projected capacitive, surface acoustic wave, piezoelectric and infra-red touching. Capacitive sensors may be disposed at a small area or over a length of the surface, such that the tapping or touching of the surface activates the monitoring device.

The memory 224 is any non-transitory tangible media, such as magnetic, optical, or electronic memory (e.g., any suitable volatile and/or non-volatile memory, such as random-access memory or a hard disk drive). The memory 224 stores the computer instructions for execution by the processor 222.

The transceiver 225 may include a separate transmitter and a separate receiver. Alternatively, the transceiver 225 may include a transmitter and receiver integrated into a single device.

In operation, the apparatus 204, utilizing the ablation contiguity engine 101, observes/obtains the biometric data of the patient 202 via the biometric sensor 221, stores the biometric data in the memory, and shares this biometric data across the system 200 via the transceiver 225. The ablation contiguity engine 101 can then utilize models, algorithms, neural networks, machine learning, and/or artificial intelligence to generate and provide mappings to physician, to reduce processing loads for the system 100, and to transform operations of the system 100 to provide more accurate mappings.

Figure 3:
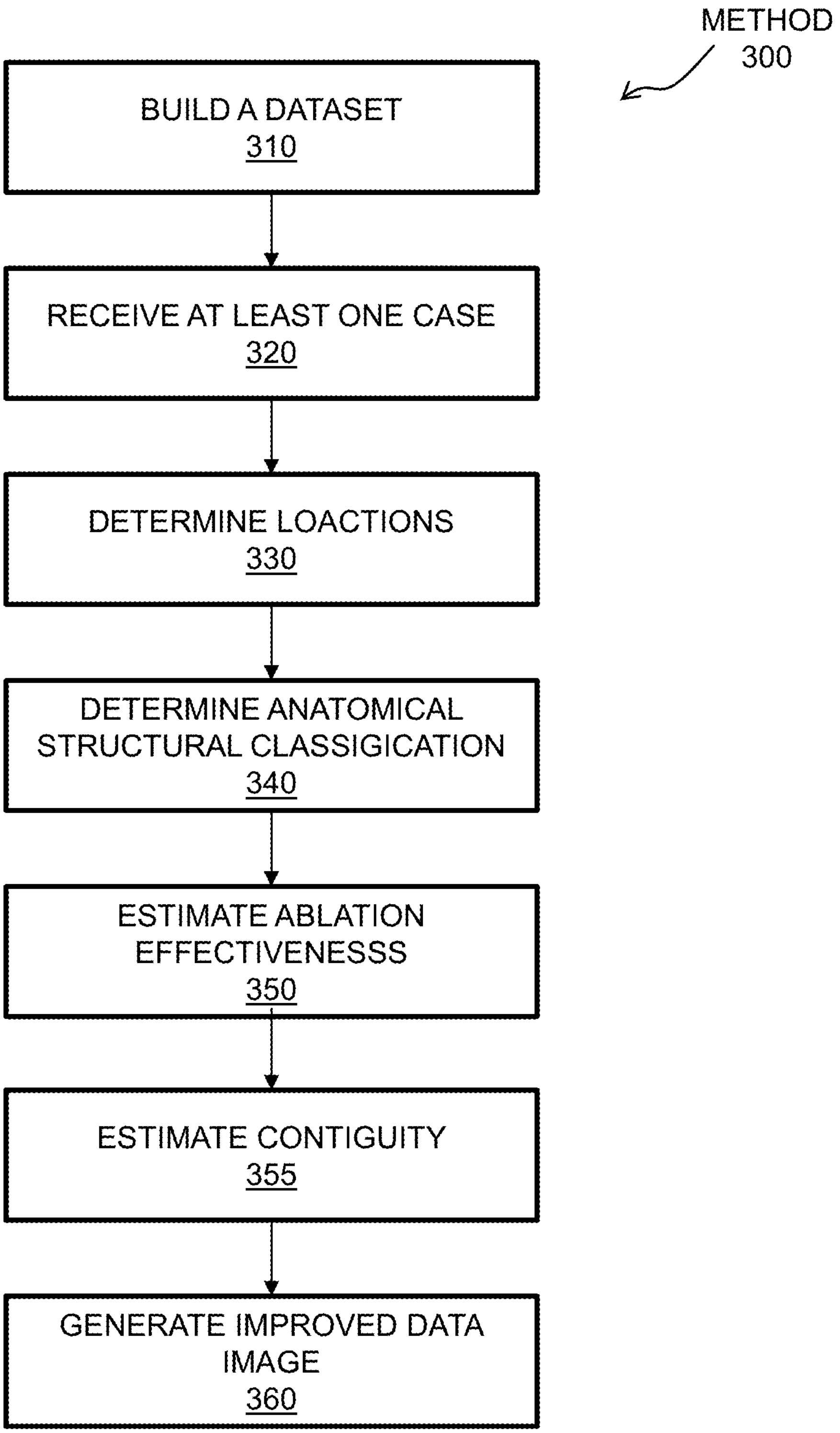
FIG. 3 illustrates a block diagram of a method according to one or more embodiments.

Turning now to FIG. 3, a method 300 (e.g., performed by the ablation contiguity engine 101 of FIG. 1 and/or of FIG. 2) is illustrated according to one or more exemplary embodiments. Any combination of software and/or hardware (e.g., the local computing device 206 and the remote computing system 208, along with the apparatus 204) can individually or collectively store, execute, and implement the ablation contiguity engine 101 and functions thereof. The method 300 addresses the shortcomings of conventional mapping methods.

In general, the ablation contiguity engine 101 provides automatic anatomical segmentation, contiguity estimation, and gap prediction for the WACA points to provide improved image data of cardiac tissue. Anatomical segmentation is an ability by the ablation contiguity engine 101 to determine in which segment of the left and right pulmonary veins that each WACA point resides. Contiguity estimation is an ability by the ablation contiguity engine 101 to determine indirect contact between the two separate circular rings around the left and right PVs and structural elements outside the left and right pulmonary veins (e.g., each ring can be evaluated separately). Gap prediction is an ability by the ablation contiguity engine 101 to determine spaces between the WACA points where PV reconnection is possible. For instance, if a gap between two ablation points is greater than a threshold value (e.g., a value along a range of 6 mm to 10 mm), then a potential site of reconnection can be declared. Further, in cases when there are no gaps between ablation points, a deeper analysis on tissue or ablation characteristics by the ablation contiguity engine 101 may predict an insufficient number of ablation points. Note that each such point is a potential location for acute or long-term reconnection. Note also that while ablation points may be part of WACA, other types of ablation can be part of the input. In this regard, the ablation contiguity engine 101 can include an algorithm to determine if a set of ablation points are part of left or right WACA rings.

The process flow 300 begins at block 310, where the ablation contiguity engine 101 builds a dataset that includes annotated anatomical structures of a cardiac tissue (e.g., a human heart or the heart 120 of FIG. 1). The dataset can be built by the ablation contiguity engine 101 by collecting and manipulating raw data (e.g., source data, atomic data or primary data), whether organized and/or disorganized, in one or more data structures (e.g., data organization, management, and storage format that enables efficient access and modification) suitable for training and machine learning. For instance, the annotated anatomical structures can include three-dimensional image files that depict the human heart and verified WACA points, and the data and/or meta data within those three-dimensional image files are collected and manipulated into one or more data structures.

In accordance with one or more embodiments, training data (e.g., a dataset used for training) can be created and maintained. Training data may include manual annotations (e.g., tags on actual ablation points by physicians that mark an anatomical structure location) and/or a type of ablation. For example, one type of ablation includes acute reconnection points. After pacing, a physician identifies a reconnection location and adds an ablation point to isolate the vein. Another type of ablation includes long term reconnection (redo) ablation point. For instance, long after the case ended, the patient has atrial fibrillation and the physician decides to perform another ablation procedure. The physician identifies the actual reconnection sites (e.g., the redo points) by manually annotating the location of each ablation point (in the WACA) into 9 anatomical structures. In turn, the training data, which is used for classifying anatomical structures, includes x, y, z locations of ablation points, an actual anatomy (e.g., a mesh file or 3D visualization of the atria), and ablation properties. The training data can be used to build the dataset that is further applied in the method 300 or by the ablation contiguity engine 101.

At block 320, the ablation contiguity engine 101 receives at least one case (e.g., a case). The case can be received in real-time, during a heart mapping phase of a WACA session. The case includes WACA points mapping cardiac tissue. The case is evaluated by the ablation contiguity engine 101.

At block 330, the ablation contiguity engine 101 determines and/or estimates locations. Examples of locations include, but are not limited to, ablation line estimations and right and left WACA locations for each WACA point of the received case.

According to one or more embodiments, a sub-algorithm of the ablation contiguity engine 101 is used to automatically compare location information of the WACA points to dimensional information along an axis (e.g., using X-axis with a first range for a left location and a second range for a right location). In turn, the WACA points are divided based on the comparison.

According to one or more embodiments, the ablation contiguity engine 101 determines whether a set of points are part of one or more ablation lines. The one or more ablation lines include, but are not limited to: a left WACA line; a right WACA line; a roof line; a left carina line; a right carina line; a posterior line; an inferior line; a mitral line; an anterior line; a left atrial appendage (LAA) isolation line; a cavo tricuspid isthmus line; a superior vena cava isolation line; a substrate modification; a substrate isolation; a fractionation; and a focal.

At block 340, the ablation contiguity engine 101 determines an anatomical structural classification for each WACA point of the received case (e.g., based on manual annotations of the training data, using the dataset from block 510). Note that a WACA anatomical structure code as further described herein. According to one or more embodiments, the ablation contiguity engine 101 performs a nine anatomical structure detection based on left and right WACA lines (of block 330).

At block 350, the ablation contiguity engine 101 estimates ablation effectiveness. In this regard, the ablation contiguity engine 101 utilizes all ablation parameters and associations to an anatomical location to estimates an effectiveness of an ablation. According to one or more embodiments, the ablation contiguity engine 101 can denote the ablation effectiveness by a binary decision of 0 or 1, where 0 represent that a "bad" ablation point and 1 represents a "good" ablation point. Further, the ablation effectiveness can be denoted by a probability for the effectiveness of the ablation between 0 to 1.

At block 355, the ablation contiguity engine 101 estimates contiguity of the line connecting two (or more) ablation points. The ablation contiguity engine 101 utilizes all the information on the location and characteristics of two or more ablations (e.g., RF index, effectiveness from previous module, stability, bi-polar voltage amplitude, etc.), According to one or more embodiments, the ablation contiguity engine 101 can estimate a contiguity of the two separate circular rings around the left and right PVs. The output of this estimation can include a probability for contiguity per WACA point. Additionally, distances of each WACA point to a next ablation and a previous ablation in the ring can contribute to the "bad/good" determination.

At block 360, the ablation contiguity engine 101 generates the improved image data for the cardiac tissue being mapped (e.g., by merging the estimations of block 350 and 355 and the determinations of blocks 330 and 340). In turn, the improved image data can be used to predict acute reconnections and redo-locations, so that appropriate action can be taken (by the physician or the medical professional) during the ablation phase in real time.

In accordance with one or more embodiments, the ablation contiguity engine 101 collects data, makes automatic decisions, and receives inputs representing user modifications to the automatic decisions (e.g., a physician 115 manually changes the automatic decisions) to provide a baseline database or training dataset. In turn, the training dataset for training the ablation contiguity engine 101 increases and/or improves over time (e.g., on average every 3-6 months), and is used to train/retrain the ablation contiguity engine 101 to improve a performance thereof. In an example, the training dataset can include machine learned contiguity estimations and manual annotations on the annotated anatomical structures, as well as predictions for the ablation contiguity engine 101 (e.g., contiguity anatomical structure).

Note that the method 300 can end and/or repeat.

Figure 4:
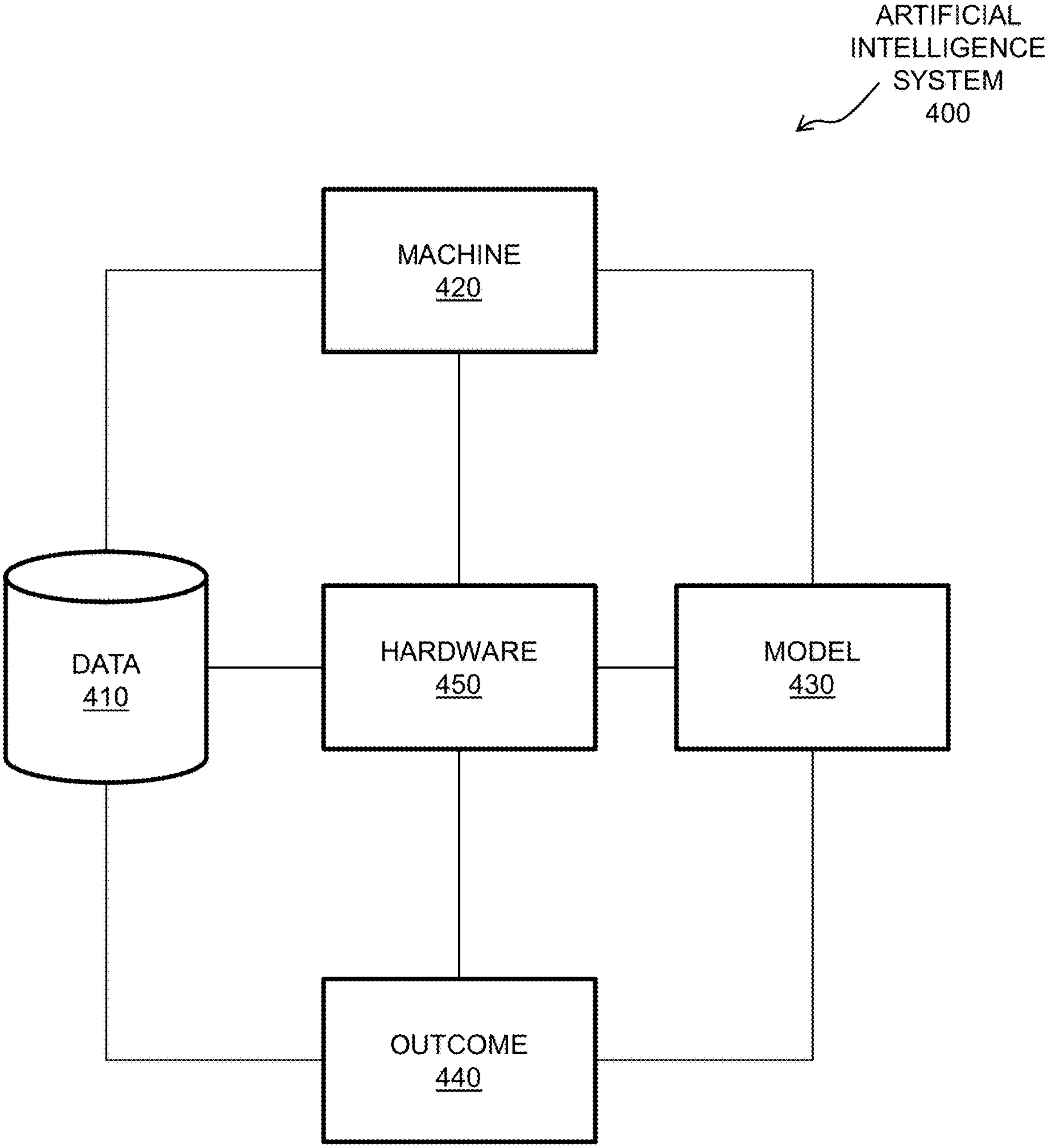
FIG. 4 illustrates a graphical depiction of an artificial intelligence system according to one or more embodiments.
Figure 5:
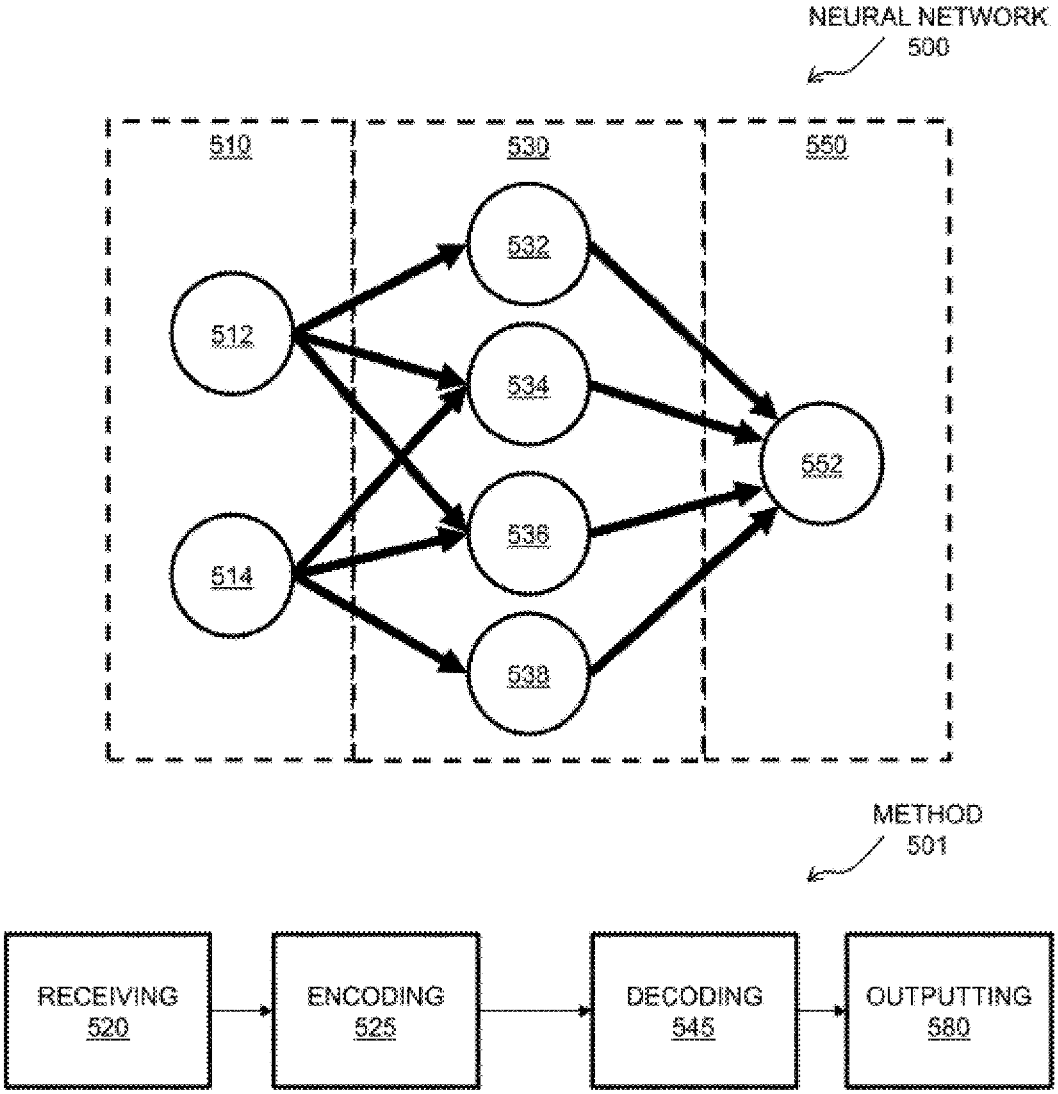
FIG. 5 illustrates an example of a neural network and a block diagram of a method performed in the neural network according to one or more embodiments.

FIG. 4 illustrates a graphical depiction of an artificial intelligence system 400 according to one or more embodiments. The artificial intelligence system 400 includes data 410 (e.g., biometric data), a machine 420, a model 430, an outcome 440, and (underlying) hardware 450. The description of FIGS. 4-5 is made with reference to FIGS. 1-3 for ease of understanding where appropriate. For example, the machine 410, the model 430, and the hardware 450 can represent aspects of the ablation contiguity engine 101 of FIGS. 1-2 (e.g., machine learning and/or an artificial intelligence algorithm therein), while the hardware 450 can also represent the catheter 110 of FIG. 1, the console 160 of FIG. 1, and/or the apparatus 204 of FIG. 2. In general, the machine learning and/or the artificial intelligence algorithms of the artificial intelligence system 400 (e.g., as implemented by the ablation contiguity engine 101 of FIGS. 1-2) operate with respect to the hardware 450, using the data 410, to train the machine 420, build the model 430, and predict the outcomes 440. Further, it should be understood that ablation contiguity engine 101 can be implemented as or with respect to the data 410, the machine 420, the model 430, the outcome 440, and any (underlying) hardware 450.

For instance, the machine 420 operates as the controller or data collection associated with the hardware 450 and/or is associated therewith. The data 410 (e.g., the biometric data as described herein) can be on-going data or output data associated with the hardware 450. The data 410 can also include currently collected data, historical data, or other data from the hardware 450; can include measurements during a surgical procedure and may be associated with an outcome of the surgical procedure; can include a temperature of the heart 140 of FIG. 1 collected and correlated with an outcome of a heart procedure; can include ablation information and determinations as to whether redo procedures are required; and can be related to the hardware 450. The data 410 can be divided by the machine 420 into one or more subsets.

Further, the machine 420 trains, such as with respect to the hardware 450. This training can also include an analysis and correlation of the data 410 collected. For example, in the case of the heart, the data 410 of temperature and outcome may be trained to determine if a correlation or link exists between the temperature of the heart 140 of FIG. 1 during the heart procedure and the outcome. In accordance with another embodiment, training the machine 420 can include self-training by the ablation contiguity engine 101 of FIG. 1 utilizing the one or more subsets. In this regard, the ablation contiguity engine 101 of FIG. 1 learns to detect case classifications on a point by point basis.

Moreover, the model 430 is built on the data 410 associated with the hardware 450. Building the model 430 can include physical hardware or software modeling, algorithmic modeling, and/or the like that seeks to represent the data 410 (or subsets thereof) that has been collected and trained. In some aspects, building of the model 430 is part of self-training operations by the machine 420. The model 430 can be configured to model the operation of hardware 450 and model the data 410 collected from the hardware 450 to predict the outcome 440 achieved by the hardware 450. In accordance with one or more embodiments, the model 430, with respect to the ablation contiguity engine 101 of FIG. 1, may receive at least a plurality of WACA points arranged/configured in two separate circular rings respective to cardiac tissue of a patient, estimate contiguity of the two separate circular rings to generate a contiguity estimation, and provide the contiguity estimation with the each of the WACA points to support treatment of the cardiac tissue.

The operation of predicting the outcomes 440 (of the model 430 associated with the hardware 450) can utilize a trained model 430. For example and to increase understanding of the disclosure, in the case of the heart, if the temperature during the procedure that is between 36.5 degrees Celsius and 37.89 degrees Celsius (i.e., 97.7 degrees Fahrenheit and 100.2 degrees Fahrenheit) produces a positive result from the heart procedure, the outcome 440 can be predicted in a given procedure using these temperatures. Thus, using the outcome 440 that is predicted, the machine 420, the model 430, and the hardware 450 can be configured accordingly.

Thus, the machine learning and/or the artificial intelligence algorithms of the artificial intelligence system 400 can include neural networks to operate with respect to the hardware 450, to use the data 410, to train the machine 420, to build the model 430, and to predict the outcomes 440. In general, a neural network is a network or circuit of neurons, or in a modern sense, an artificial neural network (ANN), composed of artificial neurons or nodes or cells.

For example, an ANN involves a network of processing elements (artificial neurons) which can exhibit complex global behavior, determined by the connections between the processing elements and element parameters. These connections of the network or circuit of neurons are modeled as weights. A positive weight reflects an excitatory connection, while negative values mean inhibitory connections. Inputs are modified by a weight and summed using a linear combination. An activation function may control the amplitude of the output. For example, an acceptable range of output is usually between 0 and 1, or it could be −1 and 1. In most cases, the ANN is an adaptive system that changes its structure based on external or internal information that flows through the network.

In more practical terms, neural networks are non-linear statistical data modeling or decision-making tools that can be used to model complex relationships between inputs and outputs or to find patterns in data. Thus, ANNs may be used for predictive modeling and adaptive control applications, while being trained via a dataset. Note that self-learning resulting from experience can occur within ANNs, which can derive conclusions from a complex and seemingly unrelated set of information. The utility of artificial neural network models lies in the fact that they can be used to infer a function from observations and also to use it. Unsupervised neural networks can also be used to learn representations of the input that capture the salient characteristics of the input distribution, and more recently, deep learning algorithms, which can implicitly learn the distribution function of the observed data. Learning in neural networks is particularly useful in applications where the complexity of the data (e.g., the biometric data) or task (e.g., monitoring, diagnosing, and treating any number of various diseases) makes the design of such functions by hand impractical.

Neural networks can be used in different fields. Thus, for the artificial intelligence system 400, the machine learning and/or the artificial intelligence algorithms therein can include neural networks that are divided generally according to tasks to which they are applied. These divisions tend to fall within the following categories: regression analysis (e.g., function approximation) including time series prediction and modeling; classification including pattern and sequence recognition; novelty detection and sequential decision making; data processing including filtering; clustering; blind signal separation, and compression. For example, Application areas of ANNs include nonlinear system identification and control (vehicle control, process control), game-playing and decision making (backgammon, chess, racing), pattern recognition (radar systems, face identification, object recognition), sequence recognition (gesture, speech, handwritten text recognition), medical diagnosis and treatment, financial applications, data mining (or knowledge discovery in databases, "KDD"), visualization and e-mail spam filtering. For example, it is possible to create a semantic profile of patient biometric data emerging from medical procedures.

According to one or more embodiments, the neural network can implement a long short-term memory neural network architecture, a convolutional neural network (CNN) architecture, or other the like. The neural network can be configurable with respect to a number of layers, a number of connections (e.g., encoder/decoder connections), a regularization technique (e.g., dropout); and an optimization feature.

The long short-term memory neural network architecture includes feedback connections and can process single data points (e.g., such as images), along with entire sequences of data (e.g., such as speech or video). A unit of the long short-term memory neural network architecture can be composed of a cell, an input gate, an output gate, and a forget gate, where the cell remembers values over arbitrary time intervals and the gates regulate a flow of information into and out of the cell.

The CNN architecture is a shared-weight architecture with translation invariance characteristics where each neuron in one layer is connected to all neurons in the next layer. The regularization technique of the CNN architecture can take advantage of the hierarchical pattern in data and assemble more complex patterns using smaller and simpler patterns. If the neural network implements the CNN architecture, other configurable aspects of the architecture can include a number of filters at each stage, kernel size, a number of kernels per layer.

Turning now to FIG. 5, an example of a neural network 500 and a block diagram of a method 501 performed in the neural network 500 are shown according to one or more embodiments. The neural network 500 operates to support implementation of the machine learning and/or the artificial intelligence algorithms (e.g., as implemented by the ablation contiguity engine 101 of FIGS. 1-2) described herein. The neural network 500 can be implemented in hardware, such as the machine 420 and/or the hardware 450 of FIG. 4. Note that, according to one or more embodiments, the neural network 500 can be implemented in hardware and/or software. According to one or more embodiments, the neural network 500 can be an autoencoder of the ablation contiguity engine 101 that extracts intracardiac based features for classification. As indicated herein, the description of FIGS. 4-5 is made with reference to FIGS. 1-3 for ease of understanding where appropriate.

In an example operation, the ablation contiguity engine 101 of FIG. 1 includes collecting the data 410 from the hardware 450. In the neural network 500, an input layer 510 is represented by a plurality of inputs (e.g., inputs 512 and 514 of FIG. 5). With respect to block 520 of the method 501, the input layer 510 receives the inputs 512 and 514. The inputs 512 and 514 can include biometric data (e.g., data at a multiplicity of points, such as WACA points, as an initial operation). For example, the collecting of the data 410 can be an aggregation of biometric data (e.g., BS ECG data, IC ECG data, and ablation data, along with catheter electrode position data), from one or more procedure recordings of the hardware 450 into a dataset (as represented by the data 410). The plurality of inputs can be ultrasound signals, radio signals, audio signal, or a two- or three-dimensional image. More particularly, the plurality of inputs can be represented as input data (X), which is raw data recorded from the heart mapping phase of a WACA session.

At block 525 of the method 501, the neural network 500 encodes the inputs 512 and 514 utilizing any portion of the data 410 (e.g., the dataset and predictions produced by the artificial intelligence system 400) to produce a latent representation or data coding. The latent representation includes one or more intermediary data representations derived from the plurality of inputs. According to one or more embodiments, the latent representation is generated by an element-wise activation function (e.g., a sigmoid function or a rectified linear unit) of the autoencoder of the ablation contiguity engine 101 that applies a weight matrix to the input intracardiac signals and adds a bias vector to the result. Note that weights and biases of the weight matrix and the bias vector can be initialized randomly, and then updated iteratively during training As shown in FIG. 5, the inputs 512 and 514 are provided to a hidden layer 530 depicted as including nodes 532, 534, 536, and 538. The neural network 500 performs the processing via the hidden layer 530 of the nodes 532, 534, 536, and 538 to exhibit complex global behavior, determined by the connections between the processing elements and element parameters. Thus, the transition between layers 510 and 530 can be considered an encoder stage that takes the inputs 512 and 514 and transfers it to a deep neural network (within layer 530) to learn some smaller representation of the input (e.g., a resulting the latent representation).

The deep neural network can be a CNN, a long short-term memory neural network, a fully connected neural network, or combination thereof. The inputs 512 and 514 can be IC ECG, body surface ECG, or IC ECG and body surface ECG. This encoding provides a dimensionality reduction of the inputs 512 and 514. Dimensionality reduction is a process of reducing the number of random variables (of the inputs 512 and 514) under consideration by obtaining a set of principal variables. For instance, dimensionality reduction can be a feature extraction that transforms data (e.g., the inputs 512 and 514) from a high-dimensional space (e.g., more than 10 dimensions) to a lower-dimensional space (e.g., 2-3 dimensions). The technical effects and benefits of dimensionality reduction include reducing time and storage space requirements for the data 410, improving visualization of the data 410, and improving parameter interpretation for machine learning. This data transformation can be linear or nonlinear. The operations of receiving (block 520) and encoding (block 525) can be considered a data preparation portion of the multi-step data manipulation by (the autoencoder of) the ablation contiguity engine 101.

At block 545 of the method 501, the neural network 500 decodes the latent representation. The decoding stage takes the encoder output (e.g., the resulting the latent representation) and attempts to reconstruct some form of the inputs 512 and 514 using another deep neural network. In this regard, the nodes 532, 534, 536, and 538 are combined to produce in the output layer 550 an output 552, as shown in block 580 of the method 501. That is, the output layer 550 reconstructs the inputs 512 and 514 on a reduced dimension but without the signal interferences, signal artifacts, and signal noise. Examples of the output 552 include cleaned biometric data (e.g., clean/denoised version of IC ECG data or the like). For instance, the denoised version of IC ECG could be free from one or more of the following: far field reduction, power line noise, contact noise, deflection noise, baseline wonders, respiration noise, and Fluro noise. The technical effects and benefits of the cleaned biometric data include enabling more accurate monitor, diagnosis, and treatment any number of various diseases.

For instance, target data for the output layer 550 includes target data type one ventricular activity (Y1) and includes target data type two input data after far field reduction (Y2). In accordance with an embodiment, the autoencoder of the ablation contiguity engine 101 can be a denoising autoencoder to find mapping functions (f, g) such that f(X)=Y1 and g(X)=Y2. Any combination of software and/or hardware (e.g., the local computing device 206 and the remote computing system 208, along with the apparatus 204) can individually or collectively store, execute, and implement the denoising autoencoder and functions thereof. The denoising autoencoder trains the autoencoder to reconstruct an input from a corrupted version of itself to force the hidden layer (e.g., the hidden layer 530 of FIG. 5) to discover more robust features (i.e., useful features that will constitute better higher level representations of the input) and prevent it from learning a particular identity (i.e., always returning to a same value). In this regard, the denoising autoencoder encodes the input (e.g., to preserve information about the input) and reverses the effect of a corruption process stochastically applied to the input of the autoencoder.

Figure 6:
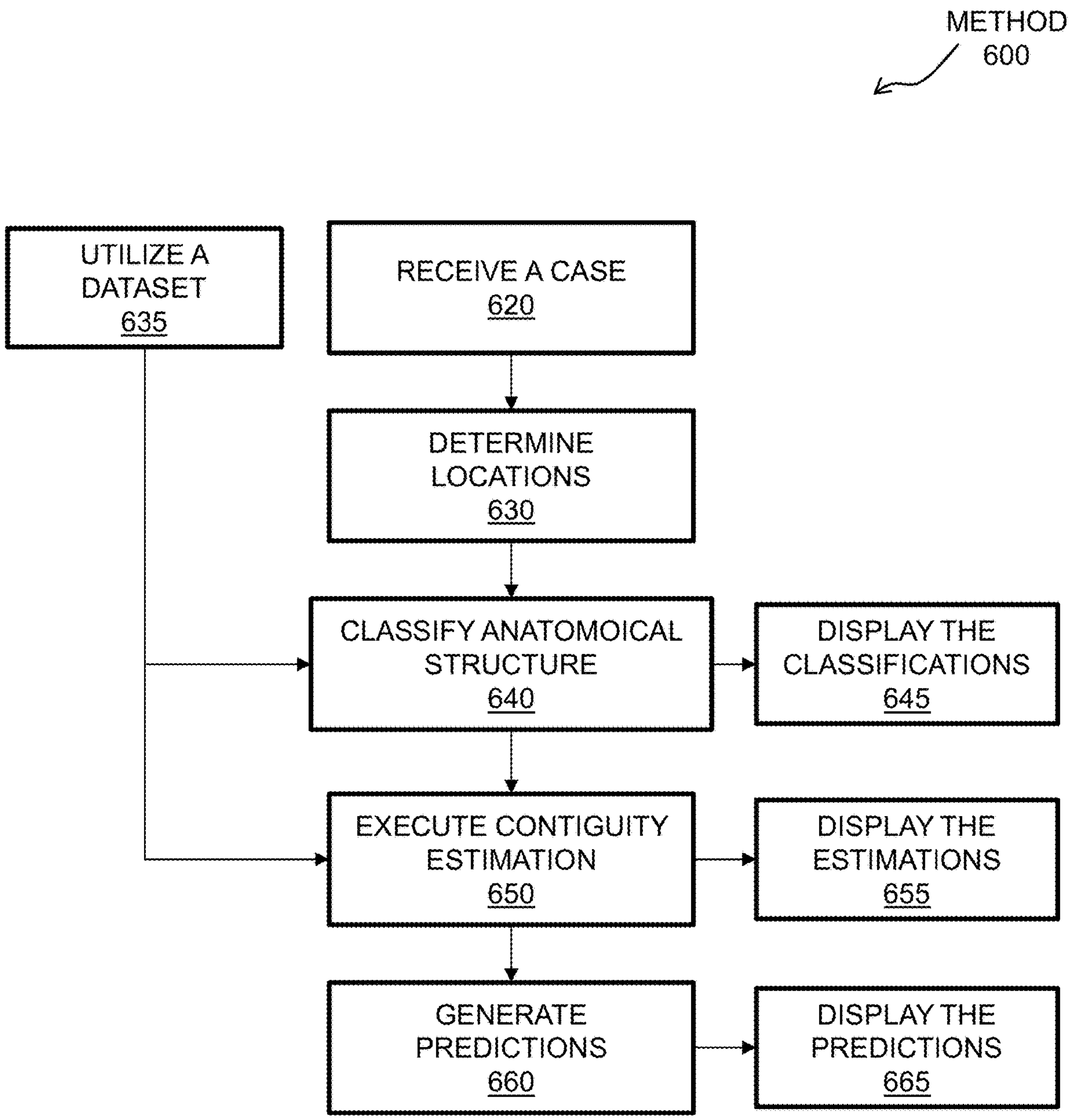
FIG. 6 illustrates an example of a neural network and a block diagram of a method performed in the neural network according to one or more embodiments.

FIG. 6 illustrates a block diagram of a method 600 according to one or more embodiments. Any combination of software and/or hardware (e.g., the local computing device 206 and the remote computing system 208, along with the apparatus 204) can individually or collectively store, execute, and implement the method 600 within the context of the ablation contiguity engine 101 and functions thereof. In general, the method 600 can be implemented with respect to a WACA treatment, which includes WACA point mapping and WACA phases. That is, implementing the method 600 respect to the WACA treatment enables a physician and/or a medical professional to more effectively treat various cardiovascular diseases with ablation itself.

For example, a catheter based WACA treatment utilizing the method 600 maps the electrical properties of the left and right PVs and provides direct information to the physician and/or the medical professional. In this regard, the mapping and the direct information includes automatic anatomical segmentation, contiguity estimation, and gap prediction for the WACA points.

The process flow 600 begins at block 620, where the ablation contiguity engine 101 receives a case. The case can be received in real-time, during the WACA point mapping phase of the WACA treatment. The case includes WACA points mapping the left and right PVs, where the WACA points themselves make two separate circular rings around the left and right PVs.

At block 630, the ablation contiguity engine 101 determines/estimates locations, such as right and left WACA locations for each WACA point of the received case and/or performs ablation line estimations.

Figure 7:
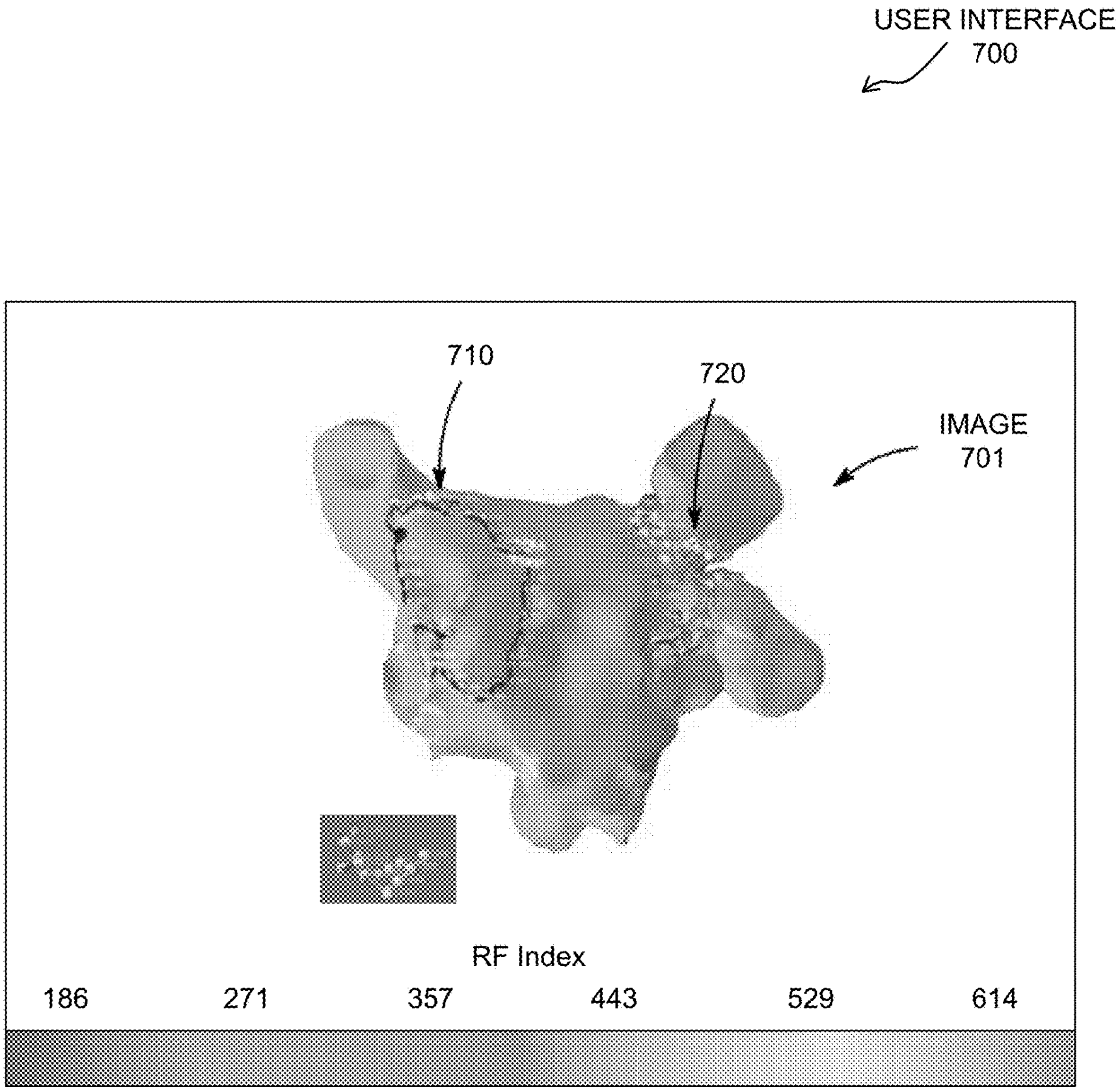
FIG. 7 illustrates an image of a user interface according to one or more embodiments.

According to one or more embodiments, the ablation contiguity engine 101 determines whether a set of points are part of one or more ablation lines. The one or more ablation lines include, but are not limited to, a left WACA line; a right WACA line; a roof line; a left carina line; a right carina line; a posterior line; an inferior line; a mitral line; an anterior line; a LAA isolation line; a cavo tricuspid isthmus line; a superior vena cava isolation line; a substrate modification; a substrate isolation; a fractionation; and a focal According to one or more embodiments, a sub-algorithm of the ablation contiguity engine 101 evaluates the WACA points to estimate left and right WACA rings. The estimation can be considered a feature extraction to determine morphological ring features. In some cases, the ablation contiguity engine 101 can automatically compare location information of the WACA points to dimensional information along an axis (e.g., using X-axis with a first range for a left location and a second range for a right location). Turning to FIG. 7, a user interface 700 provides an image 701 according to one or more embodiments. The user interface 700 is an example of a graphical user interface. The image 701 is an example of an image of the PVs with two separate circular rings 710 and 720. Each ring includes the WACA points, such as those produced in block 620.

Figure 8:
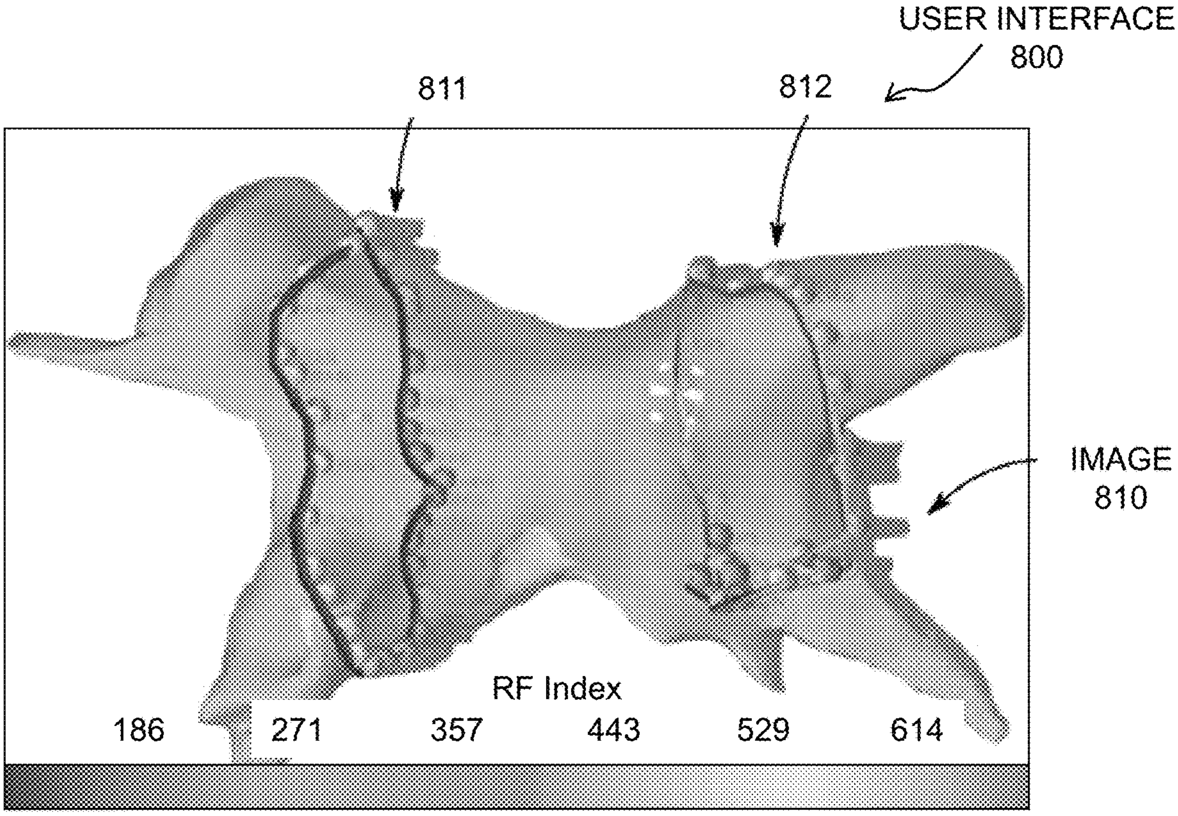
FIG. 8 illustrates user interfaces according to one or more embodiments.
Figure 8:
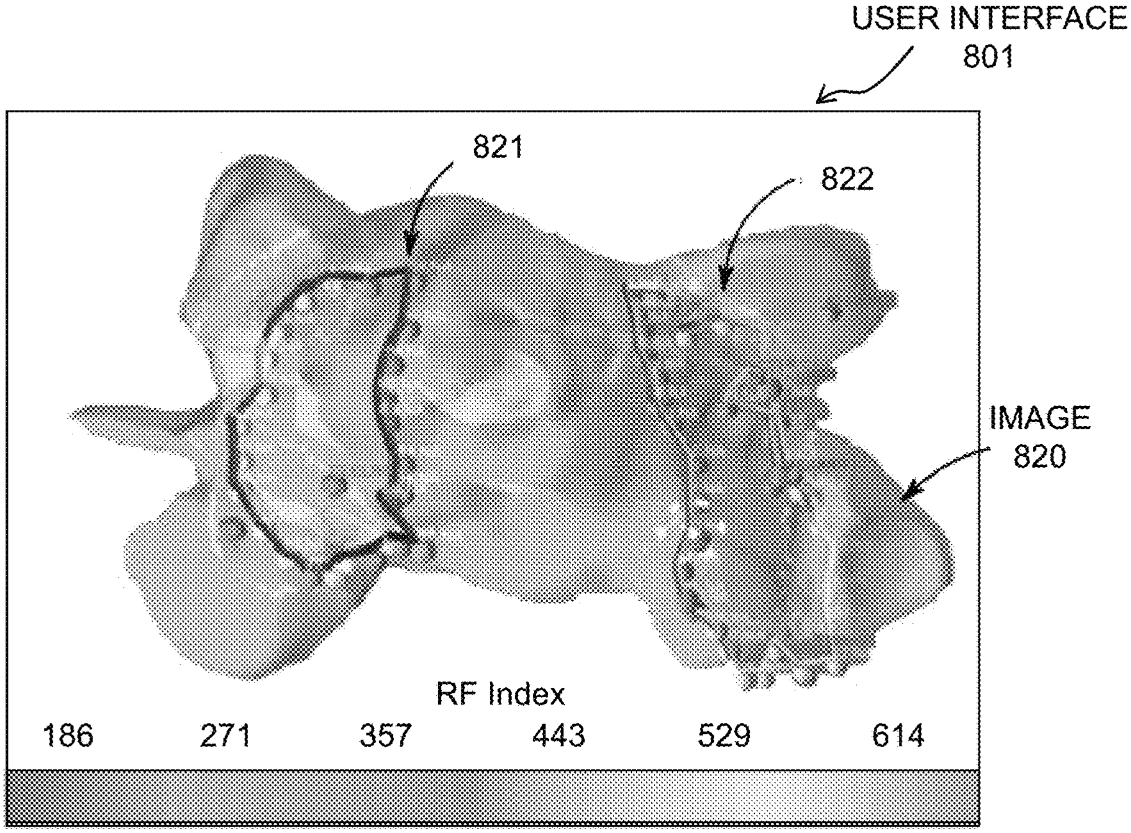

At block 635, the ablation contiguity engine 101 utilizes a dataset. In one example, the dataset includes over 1,000 or 10,000 cases, each of which comprises manual annotations and/or ablation features (e.g., RF index, force time integral (FTI); how much force is induced during an ablation point), etc.). FIG. 8 illustrates user interfaces 800 and 801 according to one or more embodiments. The user interface 800 is an example of a graphical user interface providing an image 810 with manual annotations 811 and 812 of nine anatomical structures. The user interface 801 is an example of a graphical user interface providing an image 820 with manual annotations 821 and 822 for ablation type.

At block 640, the ablation contiguity engine 101 determines an anatomical structural classification for each WACA point of the received case (e.g., based on manual annotations of the training data). Anatomical structural classification (e.g., segmentation) is an ability by the ablation contiguity engine 101 to determine in which segment of the left and right pulmonary veins that each WACA point resides. At block 645, the ablation contiguity engine 101 displays the results of the anatomical structural classification (e.g., to inform a user). In this regard, the physician or the medical personnel uses the displayed result for more effective treatment of various cardiovascular diseases.

Figure 9:
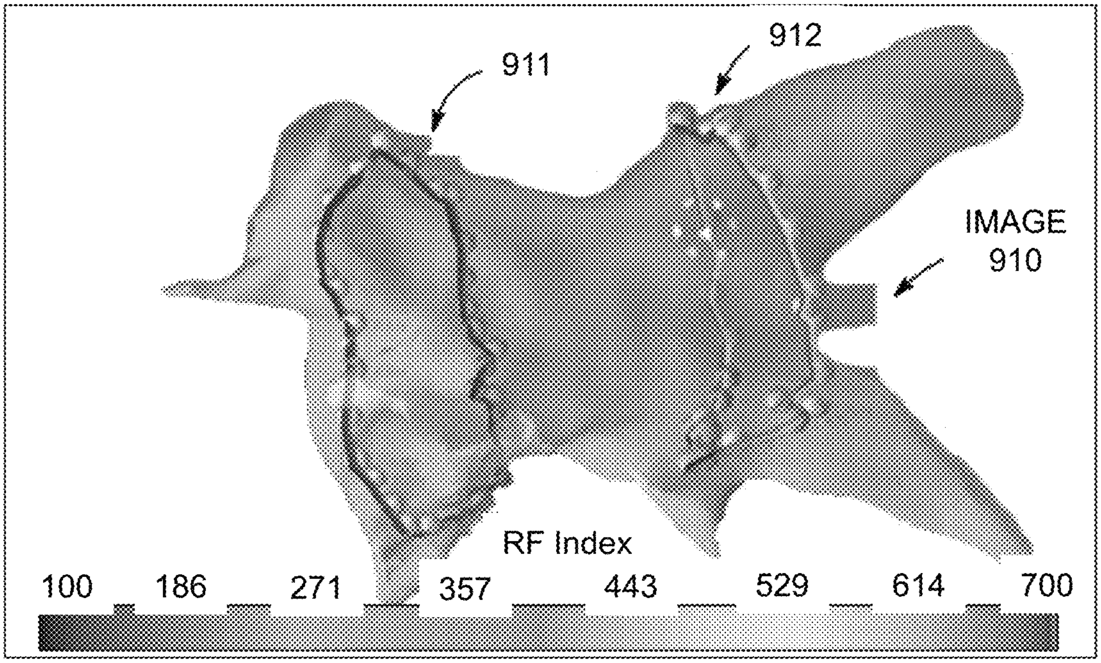
FIG. 9 illustrates a table and a user interface respective to classifying left and right WACA into anatomical structures according to one or more embodiments.
Figure 10:
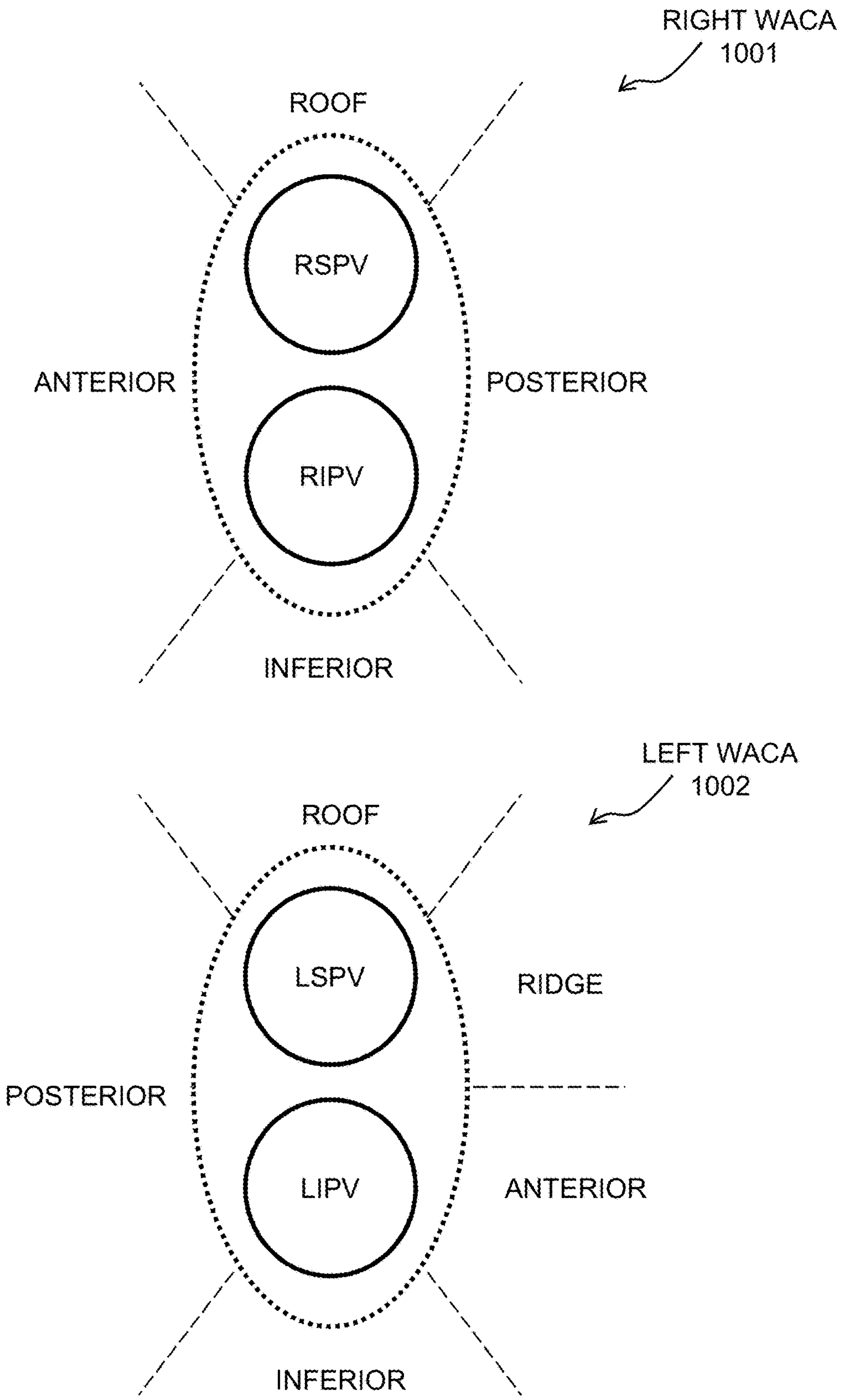
FIG. 10 illustrates diagrams of left and right anatomical structures according to one or more embodiments.

In accordance with one or more embodiments, anatomical structural classification can be defined across nine structures. Turning to FIG. 9, a table 900 illustrates nine structures or segments: right posterior, right inferior, right roof, right anterior, left posterior, left inferior, left roof, left ridge, and left anterior. Each structure or segment can be represented by a unique code, as shown in a name column of the table 900 and/or by a set of numbers (e.g., 1 to 9). FIG. 9 also shows a user interface 901 providing an image 910 (e.g., the left atria with ablation points) of classifying left and right WACA points 911 and 912 into anatomical structures by manual annotation. As shown, text of the user interface 901 represents decisions of the ablation contiguity engine 101. If the text is a first designation or color (e.g., green), the ablation contiguity engine 101 is correct. If the text is a second designation or color (e.g., red), a text with manual and algorithm anatomical structures is displayed. FIG. 10 illustrates diagrams of left and right anatomical structures (e.g., a right WACA 1001 and a left WACA 1002) according to one or more embodiments. A comparison of the table 900 of FIG. 9 to the diagrams of FIG. 10 show the nine structures or segments positioned around the right and left PVs.

Figure 11:
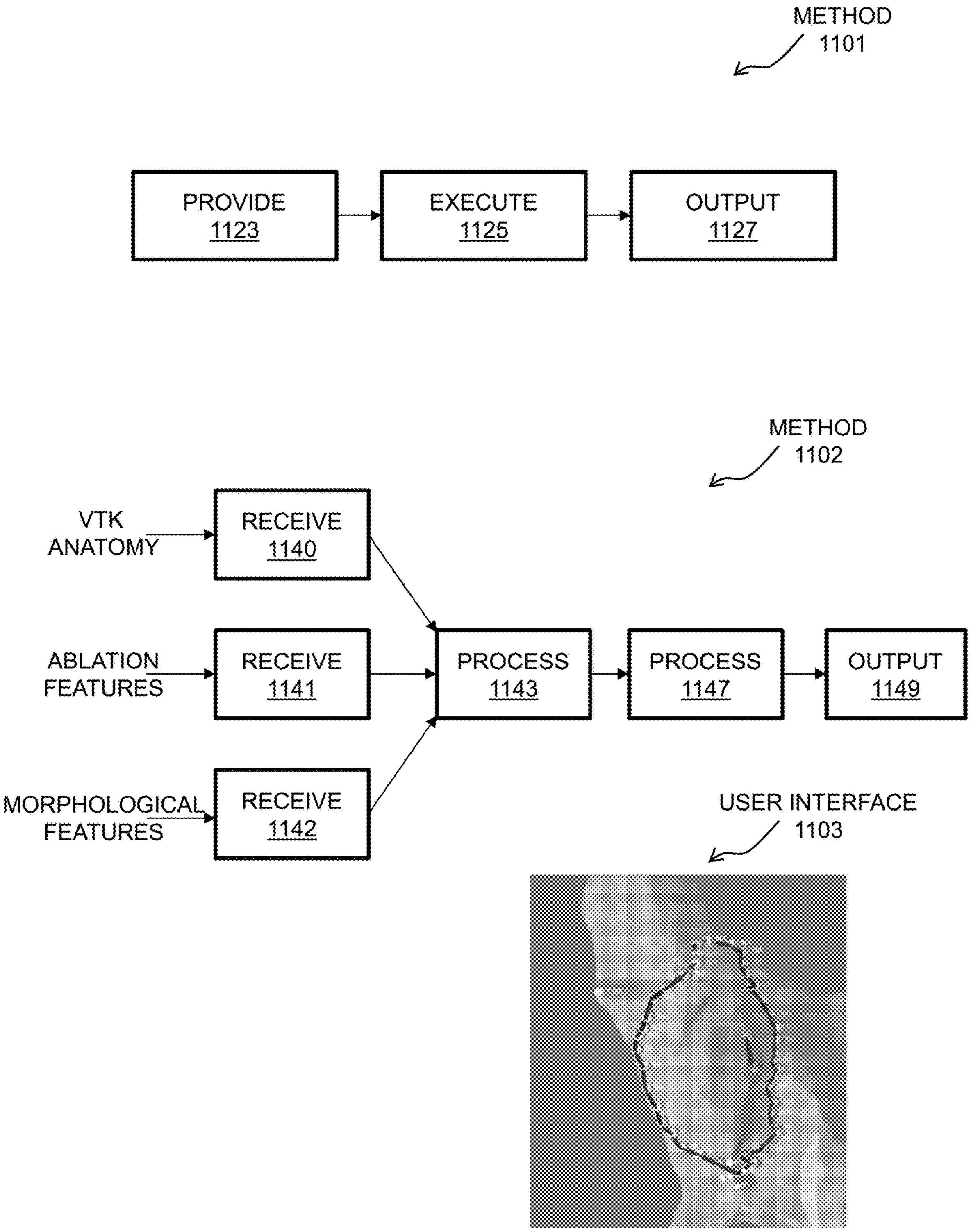
FIG. 11 illustrates block diagrams of classification methods according to one or more embodiments.

Further, in example operations of block 640, FIG. 11 illustrates block diagrams of classification methods 1101 and 1102, along with a user interface 1103 showing an image. The method 1101 is an example operation of a random forest for acute reconnection classifier (e.g., random forest classifier as described herein). The method 1102 is an example operation of a deep learning method for a redo/acute reconnection classifier. The image of the user interface 1103 depicts acute reconnection points.

The method 1101 includes providing (block 1123) morphological features, as well as ablation features, to a random forest classifier and executing (block 1125) the random forest classifier to output (block 1127) anatomy structure code (and in some cases contiguity probability). The morphological features (e.g., twenty-five different features) can be derived from the estimation and feature extraction by the sub-algorithm. In this regard, for the morphological features can be organized by the ablation contiguity engine 101 according to the left and right WACA rings. For example, as classifying anatomical structure is based on x, y, z positions of the ablation points, a sub-algorithm (of the ablation contiguity engine 101) form rings based on proximity of the ablation points. Using these rings, morphological features are extracted, such as a total surface area of a ring, how many points in the ring, an angle of each point in the ring (e.g., similar to a radial clock).

In accordance with one or more embodiments, the morphological features can be for the nine anatomical structures defined within an algorithm feature space. For instance, the algorithm feature space can include (x_left, y_left, z_left), (x_right, y_right, z_right), where the mean values of all points associated with the left and right rings; (x_norm, y_norm, z_norm), where x, y and z are normalized by range; and (x_norm_ring, y_norm_ring, z_norm_ring), where a normalized point is based on the range of the ring (left or right). The algorithm feature space can further include optional features, such as a three-dimensional surface file (e.g., a VTK file, which is a format for storing a 3D object, such as a left atria) of atrial anatomy (e.g., CNN for feature phase), mesh based features, a minimum distance of ablation points to anatomy, and ablation characteristics (e.g., power, impedance, impedance drop, stability, temperature, RF Index, FTI, features, time-based features, etc.). Note that the output of the method 1011 can be the anatomical structure code and/or a number within a set of numbers from 1 to 9.

Figure 12:
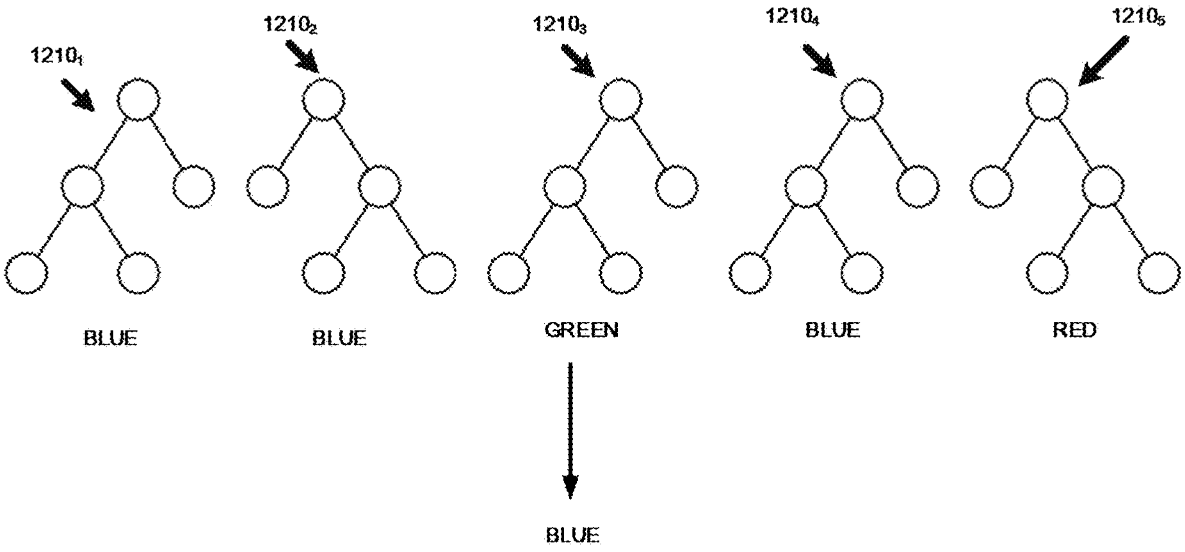
FIG. 12 illustrates an exemplary random forest classifier according to one or more embodiments.

The random forest classifier, in general, includes an ensemble learning method for classification, regression and other tasks that operate by constructing a multitude of decision trees at training time and outputting the class that is the mode of the classes or mean prediction of the individual trees. Turning to FIG. 12, an exemplary random forest classifier for classifying the color of a garment is illustrated. As illustrated in FIG. 12, the random forest classifier includes five decision trees $1210_1$, $1210_2$, $1210_3$, $1210_4$, and $1210_5$ (collectively or generally referred to as decision trees 1210). Each of the trees is designed to classify the color of the garment. In the illustration, three ($1210_1$, $1210_2$, $1210_4$) of the five trees determines that the garment is blue, while one determines the garment is green ($1210_3$) and the remaining tree determines the garment is red ($1210_5$). The random forest takes these actual predicted values of the five trees and calculates the mode of the actual predicted values to provide random forest answer that the garment is blue.

Returning to the method 1102 of FIG. 11, as discussed herein, the input to the redo/acute reconnection classifier can include a set of characteristics/features per ablation point, a 3D representation of the atria/CT scan/ultrasound/fast anatomical mapping/etc. (e.g., VTK file), and IC ECG.

The output of the redo/acute reconnection classifier can include a 1 or 0 per voxel of interest, where 1 represents an acute/long-term reconnection site. A voxel can be a point in three-dimensional space, such as a unit of graphic information (e.g., a cube of 2 mm×2 mm×2 mm). For instance, as a pixel defines a point in two dimensional space with x and y coordinates, a voxel requires a third z coordinate. According to one or more embodiments, in 3-D space, each voxel can be further defined in terms of position, color, and density. Based on the output, acute/long-term reconnection sites can be shown.

In accordance with one or more embodiments, the 3D representation of the atria can be processed using the deep CNN network to obtain the set of features, the IC ECG can be processed using deep autoencoder to obtain a set of features. Furthermore, the IC ECG can be processed to obtain additional features, such as bipolar voltage, conduction velocity, cycle length (msec), spatial temporal dispersion level, distance from focal source and fractionation level for each voxel of interest. All features (and characteristics) can be processed by a set of dense neural networks to produce contiguity predictions.

More particularly, the method 1102 includes leveraging random forest classification, fully connected dense layers, and a CNN architecture. According to one or more embodiments, the method 1102 includes leveraging random forest classification for anatomical structure classification (e.g., all classification tasks) and a CNN plus a dense layer for contiguity estimation. In this way, a five-layer CNN receives (block 1140) an anatomy of a left atria from a VTK file, a fully connected layer receives (block 1141) ablation features, and a fully connected layer receives (block 1142) morphological features, along with ablation features in some cases. For example, as described here, ablation positions (x, y, z) locations, and ablation characteristics, are processed with the VTK file using deep CNN network to obtain set of features. Then, all features are passed into a several dense layer to yield anatomical structure code. The outputs of the five layer CNN and the two fully connected layers are then passed through another two fully connected networks (e.g., processed with respect to blocks 1143 and 1147) to provide a final output of anatomy structure codes and/or contiguity probability (e.g., output with respect to block 1149).

Returning to FIG. 6, at block 650, the ablation contiguity engine 101 estimates contiguity of the two separate circular rings around the left and right PVs (e.g., acute reconnection contiguity estimation). Contiguity estimation is an ability by the ablation contiguity engine 101 to determine contact (e.g., an estimation of PV isolation; if a given ablation point is good, then contiguity estimation can isolate the vein in a radius of 3-4 mm) between the two separate circular rings around the left and right PVs and structural elements outside the left and right pulmonary veins. Note that, if stability/RF index/force are not adequate, there is likely no isolation and near this ablation point a reconnection site can be expected. The output of this estimation can include a probability for contiguity per ablation point. The probability can be a number between 0-1, as an output, where a threshold of 0.5 is used to determine 1 for outputs bigger than 0.5 (otherwise 0). At block 655, the ablation contiguity engine 101 displays the results of estimating contiguity (e.g., to inform a user). In this regard, the physician or the medical personnel uses the displayed result for more effective treatment of various cardiovascular diseases.

At block 660, the ablation contiguity engine 101 generates redo predictions (e.g., predict ablation points annotated as redo). At block 665, the ablation contiguity engine 101 displays the redo predictions results (e.g., to inform a user). In this regard, the physician or the medical personnel uses the displayed result for more effective treatment of various cardiovascular diseases.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire Examples of computer-readable media include electrical signals (transmitted over wired or wireless connections) and computer-readable storage media. Examples of computer-readable storage media include, but are not limited to, a register, cache memory, semiconductor memory devices, magnetic media such as internal hard disks and removable disks, magneto-optical media, optical media such as compact disks (CD) and digital versatile disks (DVDs), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for generating a cardiac map of at least part of a heart of a patient that improves identification of a candidate gap or acute-reconnection location during a cardiac ablation procedure, the method comprising:

receiving, in real time during the cardiac ablation procedure, sensor data from a catheter;

deriving a plurality of wide-area circumferential ablation (WACA) points from the sensor data;

determining one or more ablation lines from the WACA points;

for each WACA point, automatically classifying the WACA point into one of a plurality of predefined anatomical structures surrounding a corresponding pulmonary vein;

for each WACA point, supplying (i) ablation features associated with ablation performed at the WACA point, and (ii) morphological features associated with a patient-specific anatomical geometry at or near the WACA point, to a trained multi-layer neural network that outputs a numerical probability corresponding to an estimated contiguity or ablation effectiveness for the WACA point;

determining an estimated contiguity of the one or more ablation lines based on the numerical probabilities output for neighboring WACA points along an ablation trajectory;

identifying, as the candidate gap or acute-reconnection location, a segment of one of the ablation lines having an aggregate probability below a predefined threshold; and continuously generating and displaying, during the cardiac ablation procedure, a three-dimensional cardiac map that overlays onto the patient-specific anatomical geometry both (a) the candidate gap or acute-reconnection location and (b) a per-point color scale proportional to the numerical probability.

2. The method of claim 1, further comprising displaying the three-dimensional cardiac map via a user interface.

3. The method of claim 1, wherein the three-dimensional cardiac map includes a set of points of the one or more ablation lines.

4. The method of claim 3, wherein the one or more ablation lines comprise a left wide area circumferential ablation line and a right wide area circumferential ablation line.

5. The method of claim 1, further comprising determining right and left wide-area circumferential ablation locations, respectively corresponding to left and right pulmonary veins of the heart, wherein the three-dimensional cardiac map further includes the right and left wide area circumferential ablation locations.

6. The method of claim 1, wherein the estimated contiguity is determined using manual annotations of training data and anatomical structure classifications.

7. The method of claim 1, wherein the numerical probability comprises a probability for contiguity per WACA point.

8. The method of claim 1, further comprising receiving an intracardiac electrocardiogram, wherein the three-dimensional cardiac map further includes information from the intracardiac electrocardiogram.

9. The method of claim 1, wherein the trained multi-layer neural network comprises a deep neural network.

10. The method of claim 1, wherein supplying the ablation features and the morphological features comprises applying the ablation features and the morphological features obtained from the plurality of WACA points to a first layer of the trained multi-layer neural network.

11. A system for generating a cardiac map of at least part of a heart of a patient that improves identification of a candidate gap or acute-reconnection location during a cardiac ablation procedure, the system comprising:

a memory; and one or more processors communicatively coupled to the memory, the one or more processors collectively configured to:

receive, in real time during the cardiac ablation procedure, sensor data from a catheter;

derive a plurality of wide-area circumferential ablation (WACA) points from the sensor data;

determine one or more ablation lines from the WACA points;

for each WACA point, automatically classify the WACA point into one of a plurality of predefined anatomical structures surrounding a corresponding pulmonary vein;

for each WACA point, supply (i) ablation features associated with ablation performed at the WACA point, and (ii) morphological features associated with a patient-specific anatomical geometry at or near the WACA point, to a trained multi-layer neural network that outputs a numerical probability corresponding to an estimated contiguity or ablation effectiveness for the WACA point;

determine an estimated contiguity of the one or more ablation lines based on the numerical probabilities output for neighboring WACA points along an ablation trajectory;

identify, as the candidate gap or acute-reconnection location, a segment of one of the ablation lines having an aggregate probability below a predefined threshold; and continuously generate and display, during the cardiac ablation procedure, a three-dimensional cardiac map that overlays onto the patient-specific anatomical geometry both (a) the candidate gap or acute-reconnection location and (b) a per-point color scale proportional to the numerical probability.

12. The system of claim 11, wherein the one or more processors are further collectively configured to display the three-dimensional cardiac map via a user interface.

13. The system of claim 11, wherein the three-dimensional cardiac map includes a set of points of the one or more ablation lines.

14. The system of claim 13, wherein the one or more ablation lines comprise a left wide area circumferential ablation line and a right wide area circumferential ablation line.

15. The system of claim 11, wherein the one or more processors are further collectively configured to:

determine right and left wide area circumferential ablation locations, respectively corresponding to left and right pulmonary veins of the heart, wherein the three-dimensional cardiac map further includes the right and left wide area circumferential ablation locations.

16. The system of claim 11, wherein the estimated contiguity is determined using manual annotations of training data and anatomical structure classifications.

17. The system of claim 11, wherein the numerical probability comprises a probability for contiguity per WACA point.

18. The system of claim 11, wherein the one or more processors are further collectively configured to:

receive an intracardiac electrocardiogram, wherein the three-dimensional cardiac map further includes information from the intracardiac electrocardiogram.

19. The system of claim 11, wherein the trained multi-layer neural network comprises a deep neural network.

20. The system of claim 11, wherein supplying the ablation features and the morphological features comprises applying the ablation features and the morphological features obtained from the plurality of WACA points to a first layer of the trained multi-layer neural network.

* * * * *